United States Patent
Paris et al.

(10) Patent No.: US 12,172,179 B2
(45) Date of Patent: Dec. 24, 2024

(54) HANDHELD GAS SPRAY SYSTEM FOR MIXING AND DISPENSING MULTICOMPONENT COMPOSITIONS

(71) Applicants: BAXTER INTERNATIONAL INC., Deerfield, IL (US); BAXTER HEALTHCARE S.A., Glattpark (CH)

(72) Inventors: Spencer Scott Paris, Chicago, IL (US); Evan Joseph Mosley, Palatine, IL (US); Nikhil Mankar, Deerfield, IL (US)

(73) Assignees: Baxter International Inc., Deerfield, IL (US); Baxtter Healthcare SA, Glattpark (CH)

(*) Notice: Subject to any disclaimer, the term of this patent is extended or adjusted under 35 U.S.C. 154(b) by 1 day.

(21) Appl. No.: 18/204,506

(22) Filed: Jun. 1, 2023

(65) Prior Publication Data

US 2023/0321674 A1    Oct. 12, 2023

Related U.S. Application Data

(63) Continuation of application No. 17/405,383, filed on Aug. 18, 2021, now Pat. No. 11,697,128.

(60) Provisional application No. 63/068,666, filed on Aug. 21, 2020.

(51) Int. Cl.
*B05B 7/24* (2006.01)
*B05B 7/04* (2006.01)

(52) U.S. Cl.
CPC .......... *B05B 7/2421* (2013.01); *B05B 7/0408* (2013.01); *B05B 7/2424* (2013.01); *B05B 7/2472* (2013.01)

(58) Field of Classification Search
CPC ... B05B 7/2421; B05B 7/0408; B05B 7/2424; B05B 7/2472; B05B 7/045; B05B 7/12; B05B 7/1245; B05B 7/2467; B05B 15/55; B05B 12/0022; A61B 2017/0042; A61B 2017/004763; A61B 2017/00477; A61B 2017/00495; A61B 2017/00522; A61B 2017/00946; A61B 17/00491
See application file for complete search history.

(56) References Cited

U.S. PATENT DOCUMENTS

| | | | |
|---|---|---|---|
| 5,376,079 A | 12/1994 | Holm | |
| 5,399,159 A | 3/1995 | Chin et al. | |
| 5,582,596 A | 12/1996 | Fukunaga et al. | |
| 5,759,171 A | 6/1998 | Coelho et al. | |
| 6,059,749 A | 5/2000 | Marx | |
| 7,682,336 B2 | 3/2010 | Hoogenakker et al. | |
| 8,603,025 B2 | 12/2013 | Pongratz et al. | |
| 8,616,468 B2 | 12/2013 | Hull et al. | |
| 10,639,658 B1* | 5/2020 | Enriquez | B05B 15/55 |
| 2010/0096481 A1 | 4/2010 | Hull et al. | |
| 2011/0245866 A1 | 10/2011 | Cassingham et al. | |
| 2012/0000993 A1 | 1/2012 | Brunk et al. | |
| 2014/0364816 A1* | 12/2014 | Vogt | B05B 1/265 604/311 |
| 2015/0359857 A1 | 12/2015 | Falus et al. | |
| 2017/0086811 A1 | 3/2017 | Hull et al. | |

FOREIGN PATENT DOCUMENTS

WO    1999017833 A1    4/1999

* cited by examiner

*Primary Examiner* — Vishal Pancholi
(74) *Attorney, Agent, or Firm* — K&L Gates LLP

(57) ABSTRACT

Handheld gas spray systems for mixing and dispensing multi-component compositions.

17 Claims, 33 Drawing Sheets

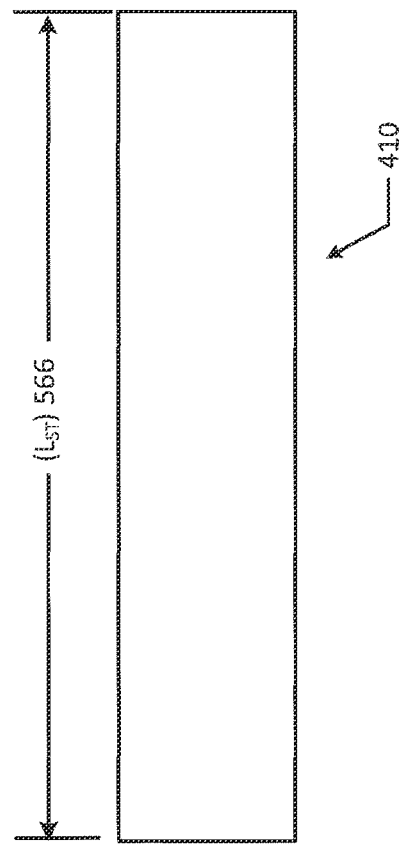
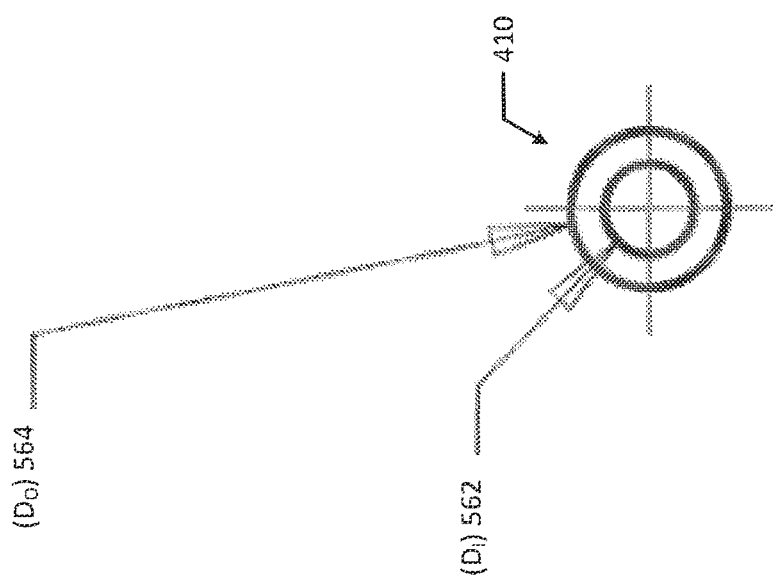
FIG. 9B
FIG. 9A

HANDHELD GAS SPRAY SYSTEM FOR MIXING AND DISPENSING MULTICOMPONENT COMPOSITIONS

RELATED APPLICATION

This application is a continuation application of U.S. application Ser. No. 17/405,383, filed Aug. 18, 2021 which claims priority from U.S. Provisional Application No. 63/068,666 filed on Aug. 21, 2020, the entirety of which is incorporated herein by reference.

BACKGROUND

Dispensing devices, such as multi-component dispensing devices are used to mix and dispense multi-component fluids. The multi-component fluids may be sealants that need to be kept separated prior to dispensing. For example, several fluid constituents may be mixed together to form a biological sealant or adhesive. Sealants and adhesives are made by mixing each fluid component together, which react with each other to harden or set after they are mixed. Often times, the two fluid components react quickly and harden into the sealant or adhesive, such as a tissue adhesive. Because of the rapid reactivity following component contact, mixing the fluid components occurs only when the multi-component fluid is ready to be dispensed and applied.

Gas systems, or systems using propellant gas are intended for the atomization and application of fibrin sealant. In order for the sealant or adhesive to properly form, each fluid component should be well mixed before applying the multi-component fluid. For example, partially mixed fluid components may result in a sealant that does not sufficiently polymerize upon application. If the multi-component fluid hardens prior to dispensing, the dispensing device clogs and prevents flow, typically requiring replacement of a portion of the dispensing device. Furthermore, ejecting hardened components or obstructions may pose a hazard for a patient and adhesive that pre-maturely clots may not adequately seal a wound. Unfortunately, existing methods for dispensing multi-component biological sealants are often inadequate.

SUMMARY

The present disclosure provides a gas spray device for mixing and dispensing two-component compositions (e.g., sealant). Gas systems may be intended for the atomization and application of fibrin sealant using a propellant gas. Such systems are able to generate a very fine mist of fibrin sealants. However, such systems typically require a hospital to maintain a supply of a large compressed gas cylinder, and often require the setup of both tubing sets and a pressure or flow regulator system, which adds to the overall setup time. Additionally, the equipment and set-up time detracts from the ease of use. The present disclosure aims to contain the source of pressurized gas in the disposable device itself, eliminating the need for an external gas source, external regulator, and any tubing set connections, thereby enhancing ease of use without compromising performance.

The handheld gas spray system disclosed herein is expected to offer comparable convenience to non-gas assisted spray devices for fibrin sealants. Additionally, the handheld gas spray system is expected to offer a spray performance (namely, very fine atomization) of more traditional gas assisted application devices. In particular, the handheld gas spray system does not rely on the use of an external gas supply and does not require maintenance of an external gas regulator. Additionally, the handheld gas spray system disclosed herein does not require the connection of tubing between such a regulator and the application device. Taken together, these advantages are expected to afford users a more convenient alternative to traditional gas-assisted applicators with a less cumbersome setup.

It is another advantage of the present disclosure to provide a dispensing device (e.g., spray applicator) that prevents cross-contamination of fluid components.

It is a further advantage of the present disclosure to provide a dispensing device (e.g., spray applicator) capable of spraying a two-component sealant, such as fibrin sealants.

Additional features and advantages of the disclosed handheld, gas-assisted, multi-component dispensing applicators, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

FIG. 9A is an elevated front view of an example sealant tube according to the present disclosure.

FIG. 9B is an elevated side view of an example sealant tube according to the present disclosure.

DETAILED DESCRIPTION OF EXAMPLE EMBODIMENTS

Figure 1A:
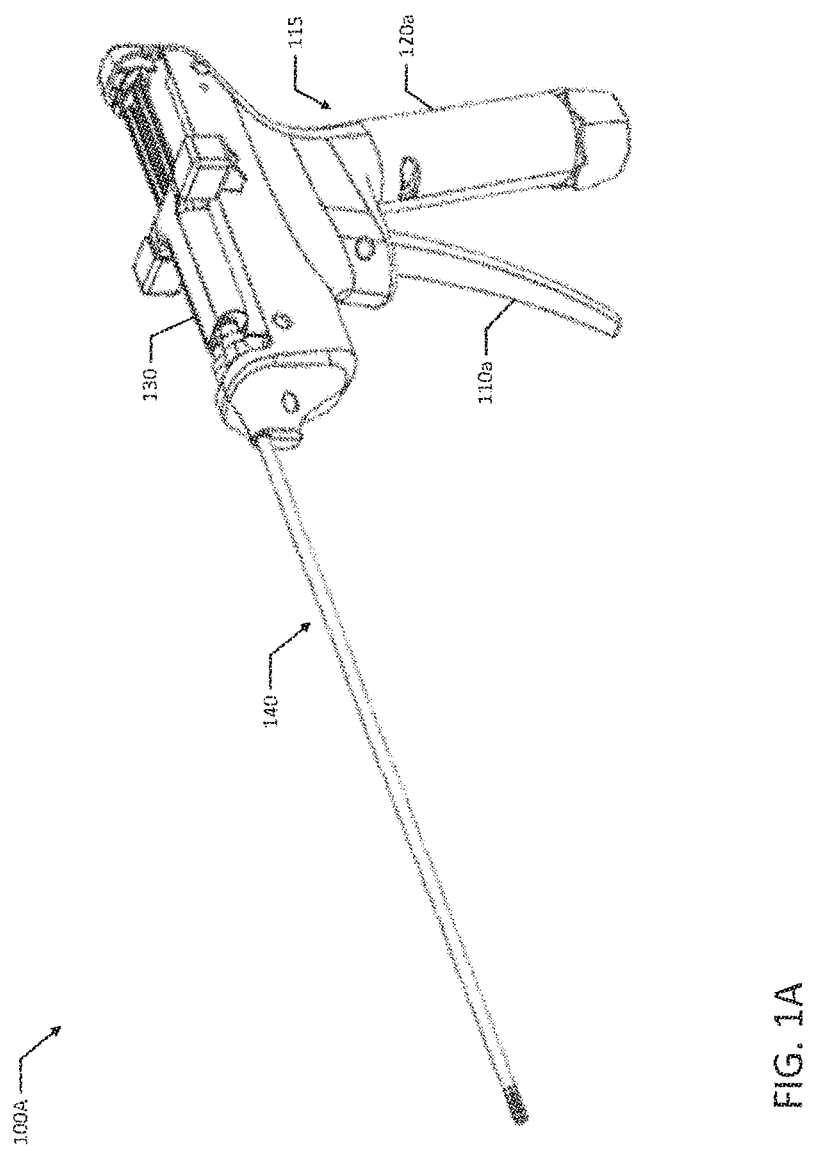
FIG. 1A is a perspective view of an example handheld gas spray system according to the present disclosure.

The handheld gas spray systems for mixing and dispensing multi-component compositions described herein provide improved dispensing devices (e.g., spray applicators) that prevent clogging and avoid cross-contamination of the components until a point of intended mixing, and are particularly useful in applying high viscosity multi-component tissue adhesives to a surgical site. For example, one way that clogging may be prevented or avoided is by ensuring that gas is the first fluid to enter the spray tip and the last fluid to exit the spray tip. Clogging and cross-contamination, such as polymerized adhesive or sealant (e.g., fibrin sealant), are problematic as they may cause injury to a patient if ejected and may not properly seal a wound or tissue. Additionally, clogging and cross-contamination may increase costs associated with dispensing applicators as a clogged device may be inoperable or may require a new dispensing tip. The multi-component dispensing applicator (e.g., a spray applicator) discussed herein improves multi-component fluid dispensing by preventing, resisting, mitigating or reducing clogging and cross-contamination.

The handheld gas spray system described herein is a sterile device and may be a single use device. A miniature gas cartridge (e.g., $CO_2$ cartridge) is contained within the handle of the device. The gas cartridge may be filled with a specified fill weight to ensure that a two-phase system of vapor and liquid in equilibrium exists when operating the handheld gas spray system within an anticipated operating temperature range. By filling the cartridge in this manner, the system may advantageously reduce the likelihood of excess mass flow through the flow restrictor due to the presence of saturated liquids when operating the system at high temperatures. Upon actuation of the device trigger by the user, $CO_2$ flows to the patient-facing end of the device. Simultaneously, two-component sealant is carried from the syringe installed on the device to the spray tip. The pressured gas and the two-component sealant mix inside of the spray tip, resulting in an atomized spray. In an example, when activation of the device trigger ceases, first the flow of the two-component sealant may stop, which may be followed by stopping flow of the gas. By providing for a flow of gas before a flow of sealant and for a period after the flow of the two-component sealant stops, clogging may be prevented or avoided or reduced or mitigated.

Pistol-Grip Spray Device

Referring to the drawings, FIGS. 1A, 1B, 1C, 1D and 1E illustrate an example embodiment of a handheld gas spray system 100A. The handheld gas spray system 100A is a direct grip or pistol grip style spray device. The handheld gas spray system 100A, which may also be referred to herein as a spray delivery device or spray applicator, includes a ratcheting trigger 110a that is provided in front of a pistol-grip handle 120a. When pulled by a user, the trigger 110a activates a gas valve (described in more detail below) and pushes the syringe 130 to deliver two-component sealant through a fluid conveyance subassembly 140 to a distal end of the handheld gas spray system 100a. Unlike the direct grip design, which is illustrated in FIGS. 2A and 2B (described in more detail below), several pulls of the trigger 110a of system 100A may be required to deliver the full contents of the syringe 130 to a surgical site. However, one advantage of the handheld gas spray system 100a illustrated in FIGS. 1A, 1B, 1C, 1D and 1E is that the ratcheting trigger 110a may provide fine control by the user in terms of incremental dispensing of the syringe contents with relatively low grip force.

Figure 1B:
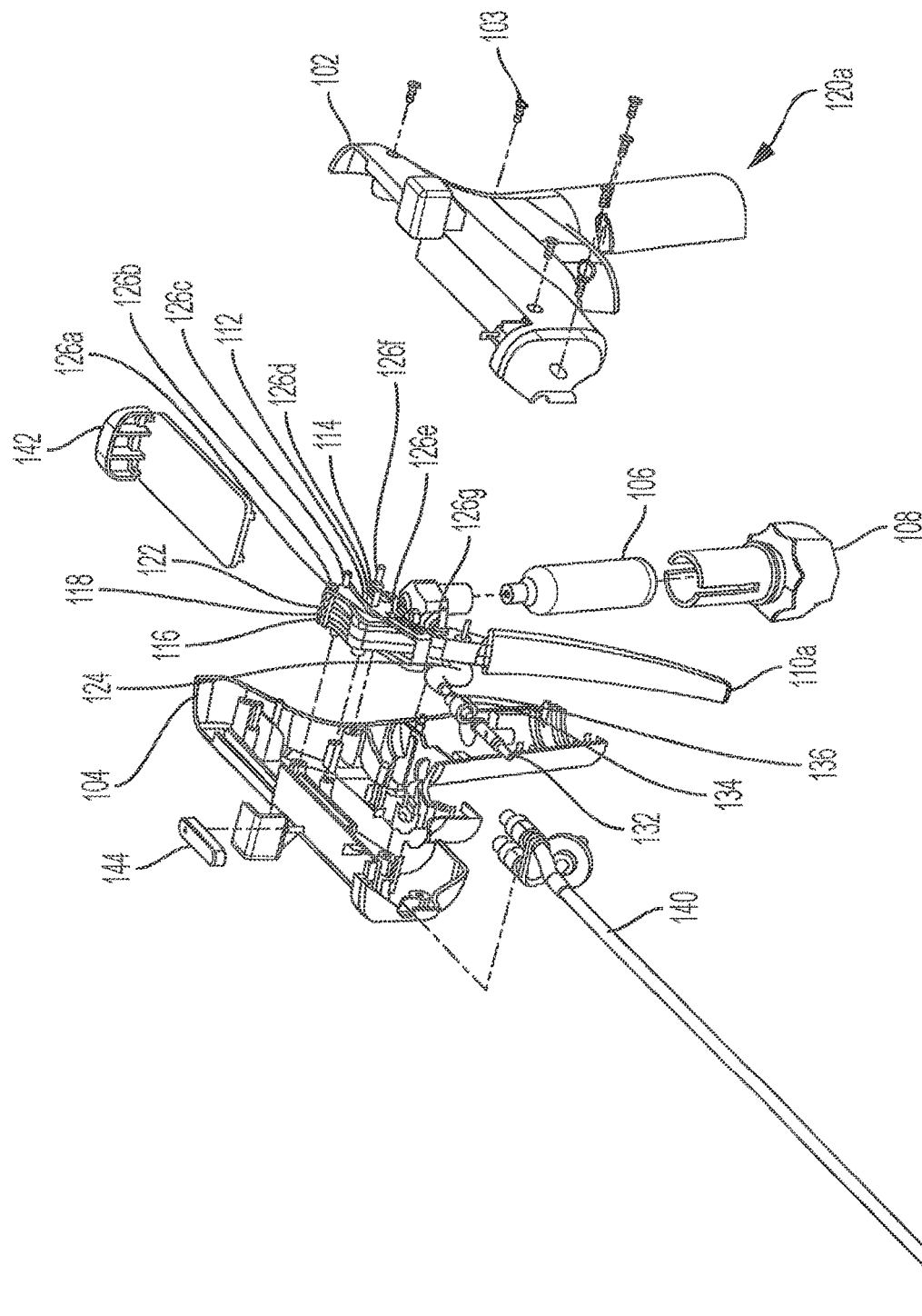
FIG. 1B is an exploded perspective view of the example handheld gas spray system of FIG. 1A.
Figure 2A:
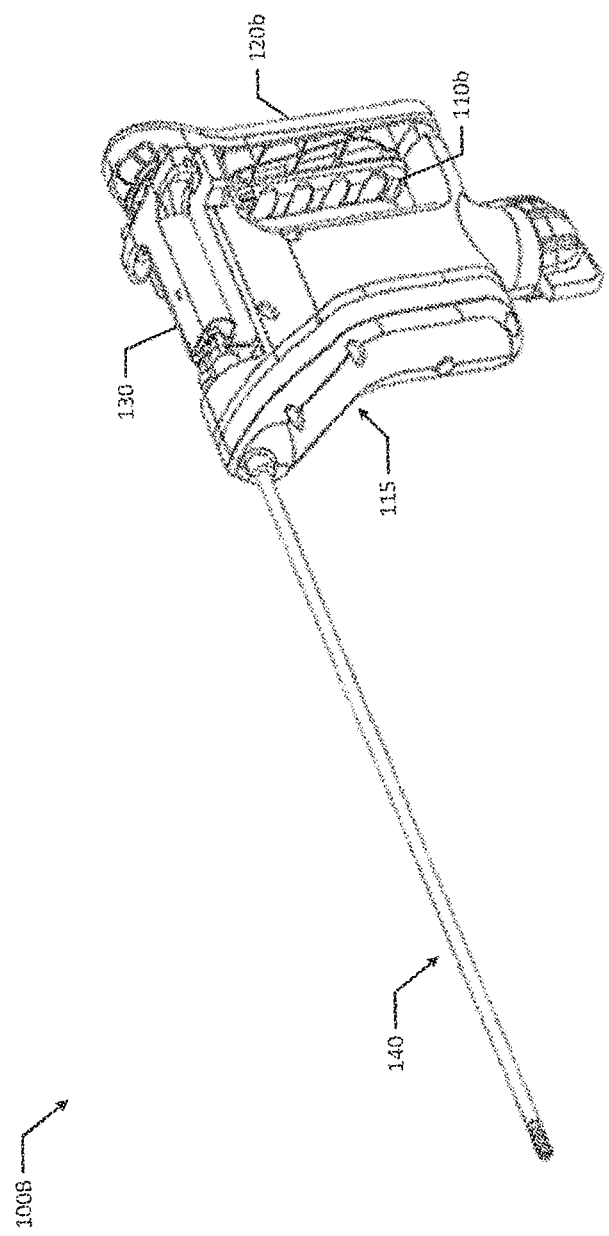
FIG. 2A is a perspective view of an example handheld gas spray system according to the present disclosure.
Figure 2B:
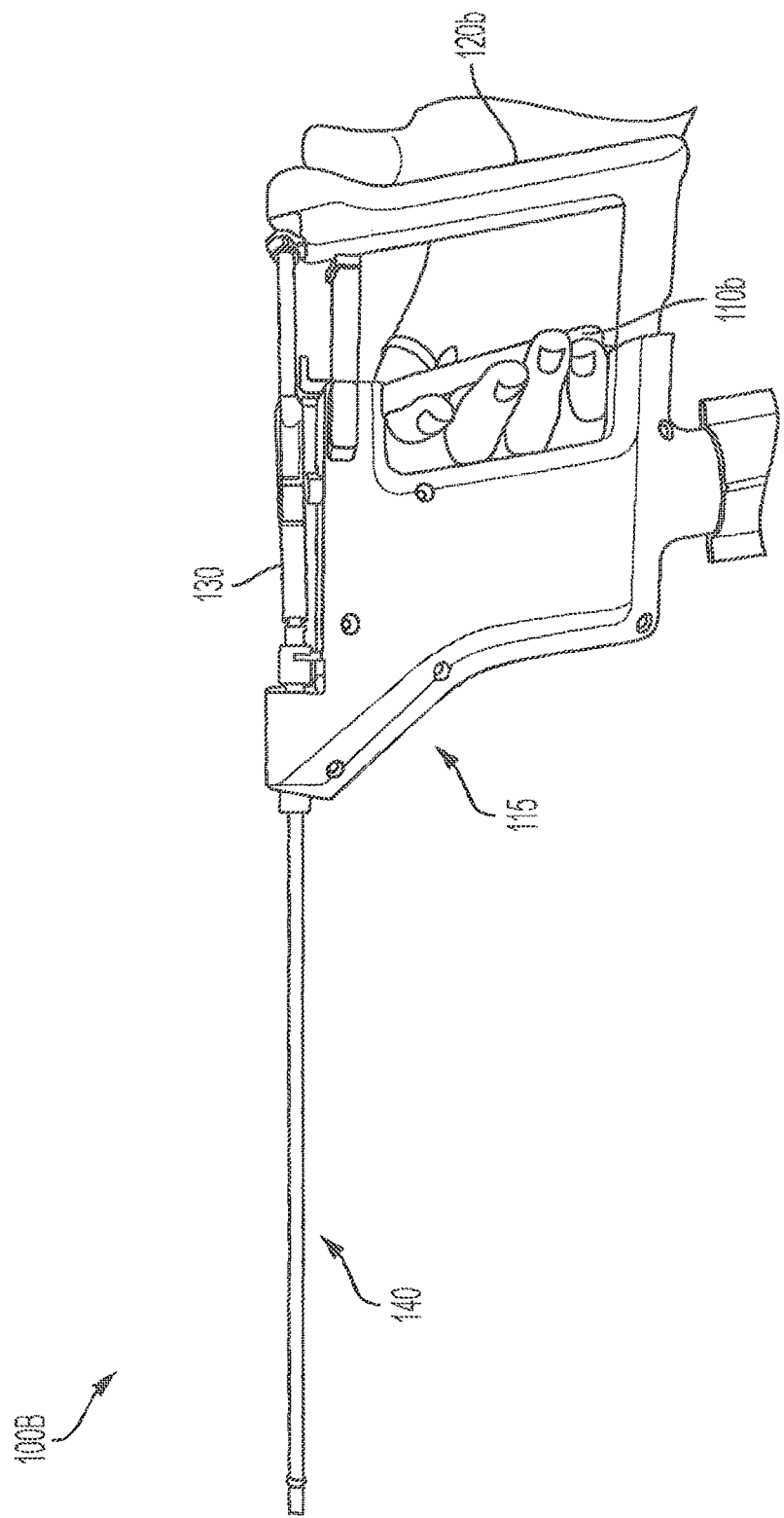
FIG. 2B is an elevated side view of the handheld gas spray system of FIG. 2A.

FIG. 1B is an exploded view of the handheld gas spray system 100A. As discussed above, the gas spray system 100A includes a trigger 110a, a housing 115 that may form a handle 120a, syringe 130, and a fluid conveyance subassembly 140. The housing 115 may include a right-hand-side casing cover 102 and a left-hand-side casing cover 104 (when viewing the system 100a from the spray tip). When casing covers 102 and 104 are joined to form the housing 115, a lower portion of the housing 115 creates handle 120a, which is adapted to house a gas cartridge 106 that is further held in place by a cartridge activator knob 108.

In the illustrated example, the casing covers 102 and 104 may be joined by screws 103, however other connectors or connection types may be possible such as a snap-fit, press-fit connection, or other plastics weldment techniques (e.g., ultrasonic welding, etc.). The casing covers 102 and 104 may be adapted to provide points for rigid assembly of the liquid conveyance subassembly 140 and gas valve subassembly (discussed in more detail below) within the system 100A. The cartridge activator knob 108 may be captured within the lower portion of the housing 115 (e.g., lower portions of covers 102 and 104), which allows rotation/translation of a gas cartridge 106 (e.g., $CO_2$ cartridge) contained within the housing 115. Additionally, the cartridge activator knob 108 and housing 115 are also adapted to prevent outright removal of the gas cartridge 106 from the system 100A.

The gas spray system 100A may also include a cam lever 112, a gas lever 114, a ratchet arm 116, and a pawl 118 that work in conjunction with a pawl torsional spring 122 and a trigger torsional spring 124. The various components above may be mechanically linked via dowel pins 126a-g, hereinafter referred to generally as dowel pin(s) 126. The gas spray system 100a may also include a pressure relief valve 132 in communication with a connector 134 and a tube 136 that is in fluid communication with the gas source or gas cartridge 106. In an example, the connector 134 is a male Luer lock to barb connector.

Figure 14B:
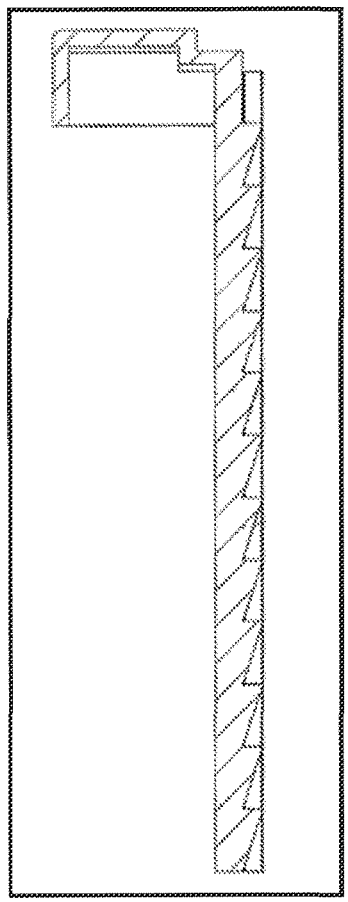
FIGS. 14A to 14F illustrate additional views of example components of the handheld gas spray system(s) described herein.

Additionally, the gas spray system 100A may include a slider rack 142 mechanically linked to the trigger to depress the syringe plunger and a spacer 144 to physically constrain a syringe of smaller bore size in the vertical direction. The slider rack 142 is further illustrated in FIGS. 14A and 14B, which illustrate ratcheting features (e.g., notches or teeth) on the bottom of the slider rack 142 that are adapted to assist with depressing the syringe plunger.

Figure 1C:
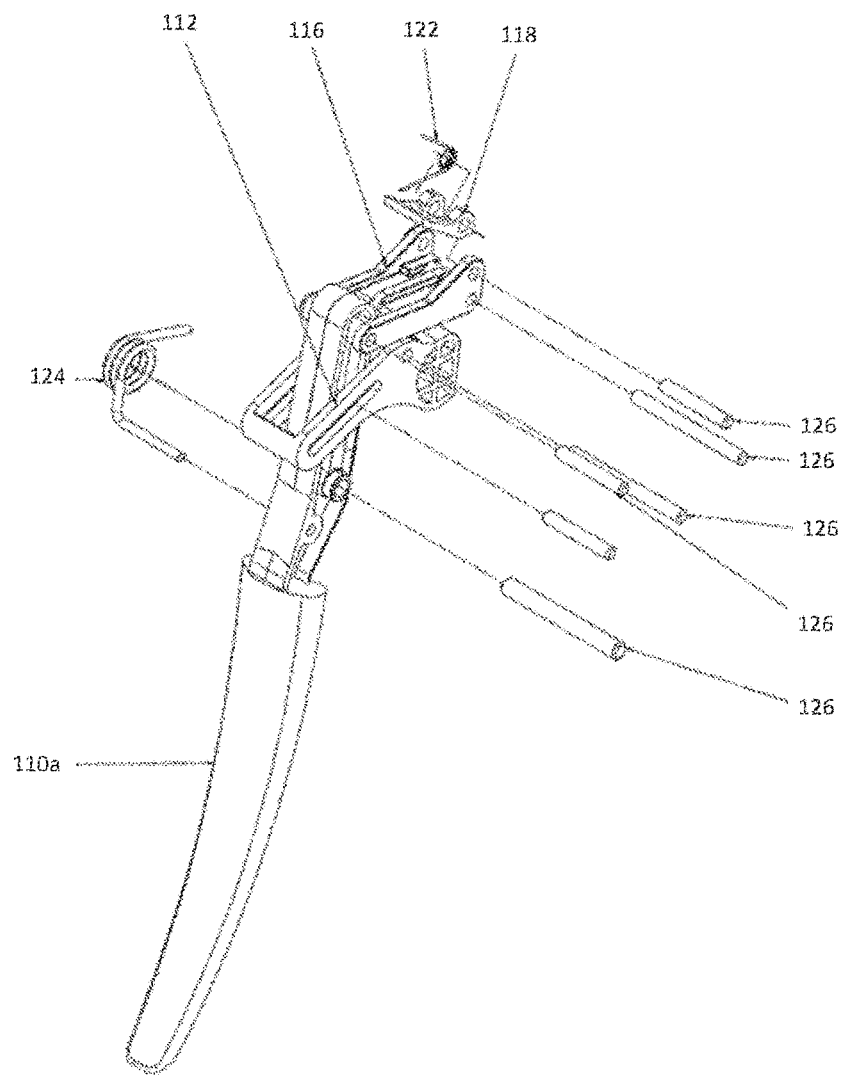
FIG. 1C is an exploded perspective view of a trigger assembly according to the present disclosure.
Figure 1D:
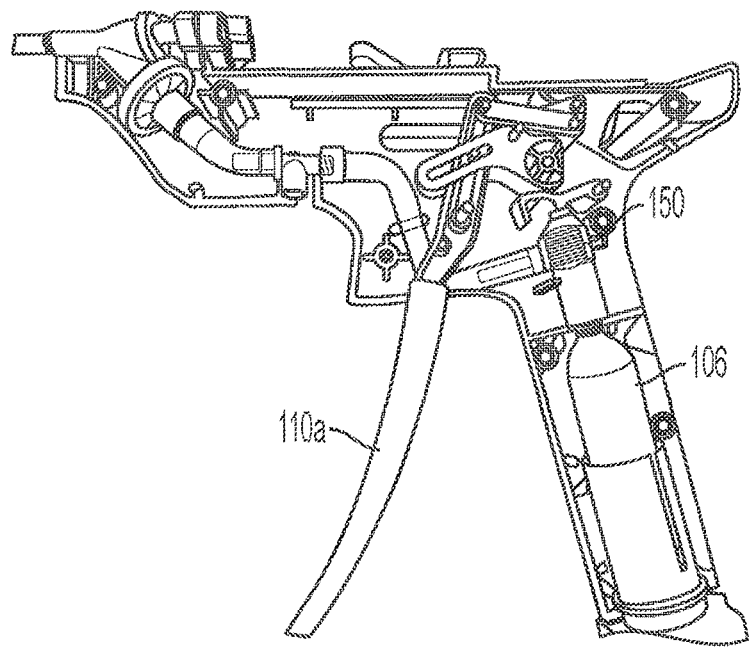
FIG. 1D is an elevated side view of a portion of an example handheld gas spray system according to the present disclosure.
Figure 1E:
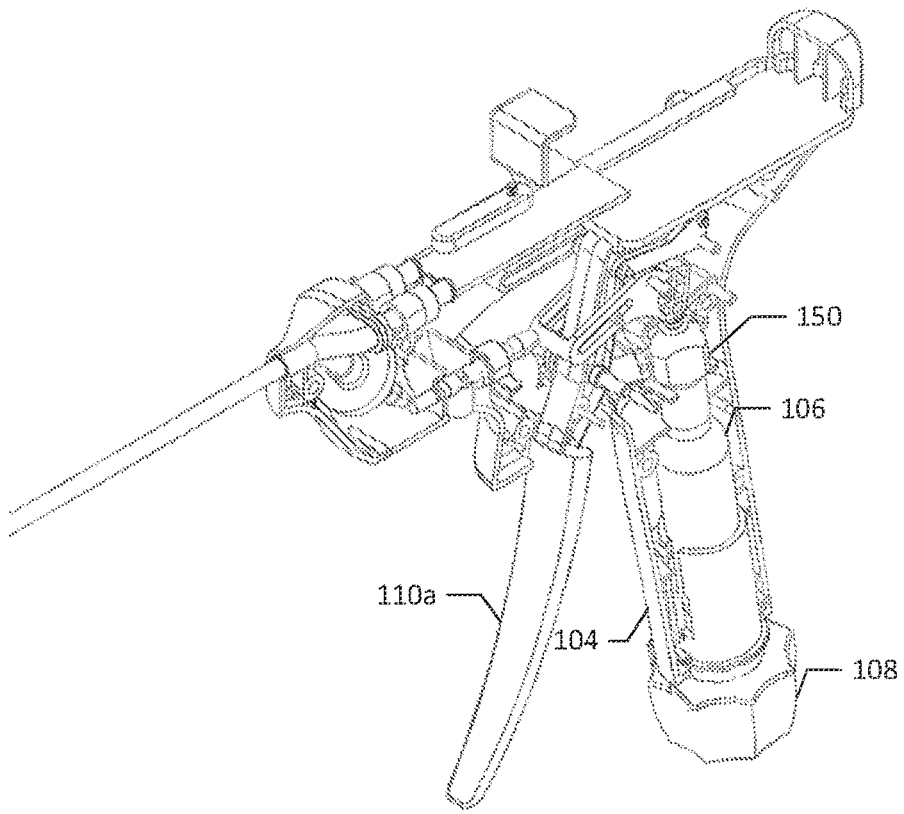
FIG. 1E is a perspective view of a portion of an example handheld gas spray system according to the present disclosure.

FIG. 1C illustrates additional details of the trigger assembly, which is a linked series of components located inside of the device handle 120a and that are provided to connect the trigger 110a to both a gas valve assembly 150 (as illustrated in FIGS. 1D and 1E) and the syringe 130 (e.g., sealant syringe). As discussed above, the trigger assembly includes trigger 110a, a cam lever 112, a ratchet arm 116, and a pawl 118 that work in conjunction with a pawl torsional spring 122 and a trigger torsional spring 124. As discussed above, the various components of the trigger assembly may be mechanically linked via dowel pins 126. A small displacement of the trigger 110a rotates cam lever 112 to fully activate the gas valve assembly 150 into its open state. Under additional displacement, the ratchet arm 116 and pawl 118, which may form a ratchet/pawl subassembly, moves along a track, engaging a rack (not pictured). The additional displacement also moves the rack along its track formed within the casing covers 102 and 104. For example, the track may be formed on the inside of casing covers 102 and 104. As the trigger 110a travels toward the pistol grip handle 120a, the gas remains on while the rack compresses the syringe 130 by an incremental amount, delivering a portion of the sealant contained within syringe 130 in spray form. As noted above, to reduce or prevent clogging, the gas may remain on for a period of time after compression of the syringe 130 ceases. For example, gas may remain on by continuing to hold the trigger 110a in the actuated position for a period of time sufficient to clear residual sealant from the spray tip.

Direct Grip Spray Device

Figure 2C:
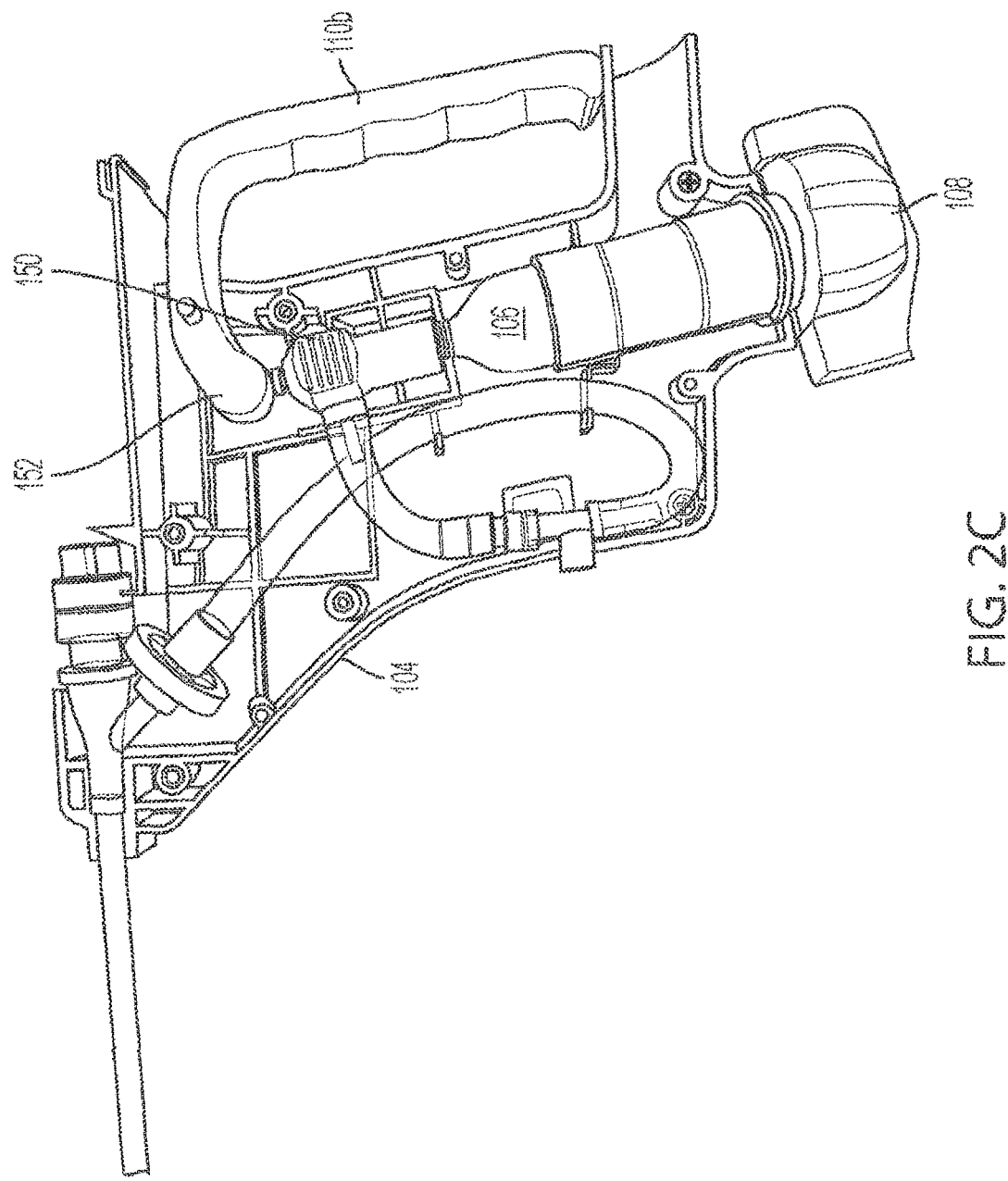
FIG. 2C is an elevated side view of a portion of an example handheld gas spray system according to the present disclosure.

Another example embodiment of a handheld gas spray system 100B is illustrated in FIGS. 2A, 2B and 2C. The handheld gas spray system 100B includes a handle 120b on a rear portion of the device, which slides when compressed by the user, pushing on the loaded syringe 130 to deliver the two-component sealant through a fluid conveyance subassembly 140. As the handle 120b slides when compressed, the user's grip simultaneously activates a trigger 110b to open a gas valve, allowing gas to flow to the distal end of the device to atomize the sealant. The user may continuously grip the system 100B, which may also be referred to herein as a spray delivery device or spray applicator, until the entire contents of the syringe 130 have been expelled or may pause application and deliver in several short bursts.

Similar to system 100A, the housing 115 of system 100b may include a right-hand-side casing cover 102 and a left-hand-side casing cover 104. The casing covers 102 and 104 may be adapted to provide points for rigid assembly of the liquid conveyance subassembly 140 and gas valve subassembly (discussed in more detail below) within the system 100B. Similarly, system 100B may include a cartridge activator knob 108. The cartridge activator knob 108 may be captured within the lower portion of the housing 115 (e.g., lower portions of covers 102 and 104), which allows rotation/translation of a gas cartridge 106 (e.g., $CO_2$ cartridge) contained within the housing 115. Additionally, the cartridge activator knob 108 and housing 115 are also adapted to prevent outright removal of the gas cartridge 106 from the system 100b. The handle 120b at the rear of the system 100b is adapted to slide along a track formed on the inside of casing covers 102 and 104. System 100b may also include a mechanical stop that prevents removal of the handle 120b from the device.

FIG. 2B illustrates system 100b with the trigger 110b and handle 120b extended away from each other. The trigger 110b features two round bosses coaxially opposed on its left and right sides which mate rotatably with bores provided by the casing covers 102 and 104, allowing rotation about a fixed axis. Specifically, as illustrated in FIG. 2C, the trigger 110b is provided to be gripped by the user's fingers. Additionally, the trigger 110b features a cam 152 which depresses a valve stem (not pictured here, but see valve stem 204 of FIGS. 3A, 3B and 3C) of the gas valve assembly 150, thereby opening the gas valve to activate gas flow. The handle 120b at the rear of the device simultaneously moves, delivering sealant to the spray tip to be mixed with gas. The pivot position of trigger 110b may be adjusted to ensure that the force required to actuate the gas valve does not exceed the force required to dispense sealant from the loaded syringe, allowing gas to be activated before and after delivery of sealant spray to aid in clearing of residual sealant from the device spray tip.

Figure 2D:
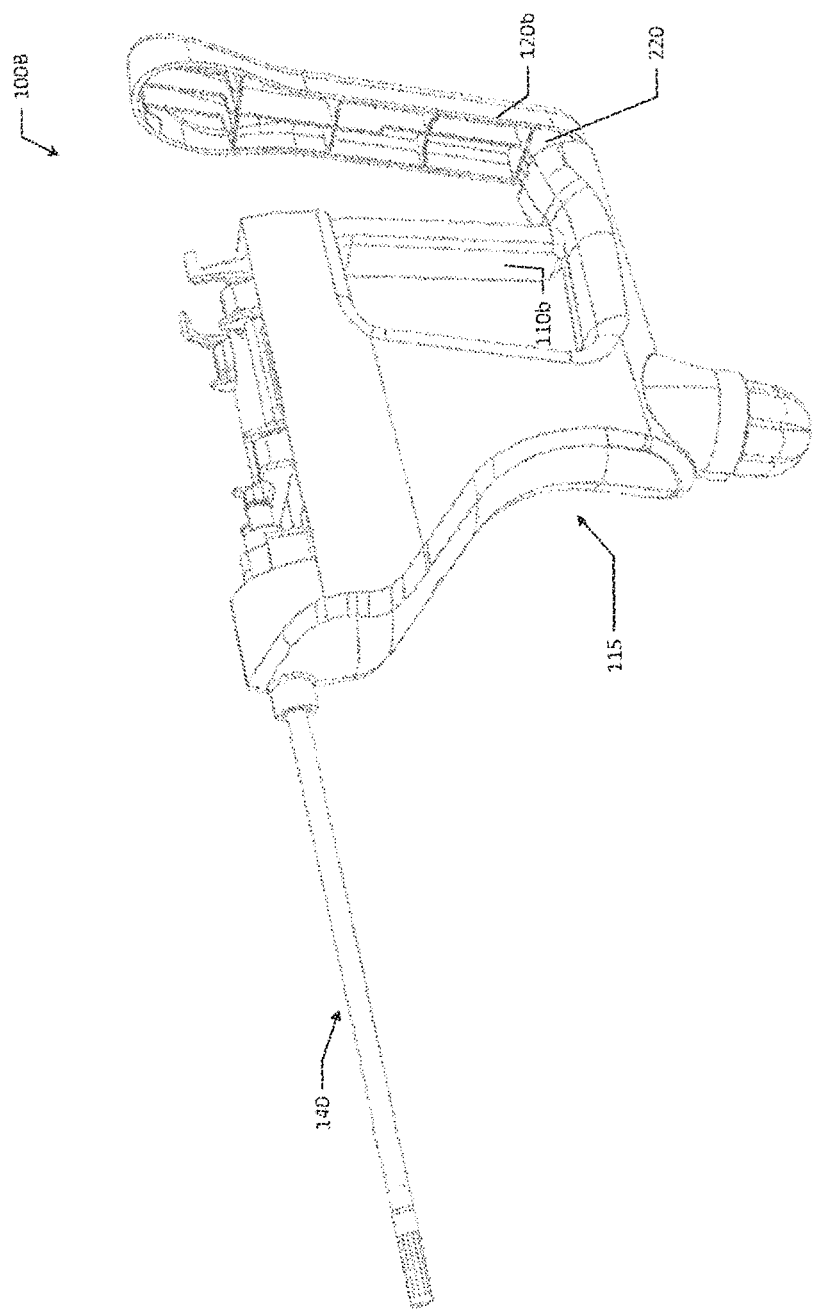
FIG. 2D is a perspective view of an alternate embodiment of an example handheld gas spray system, according to the present disclosure.
Figure 2E:
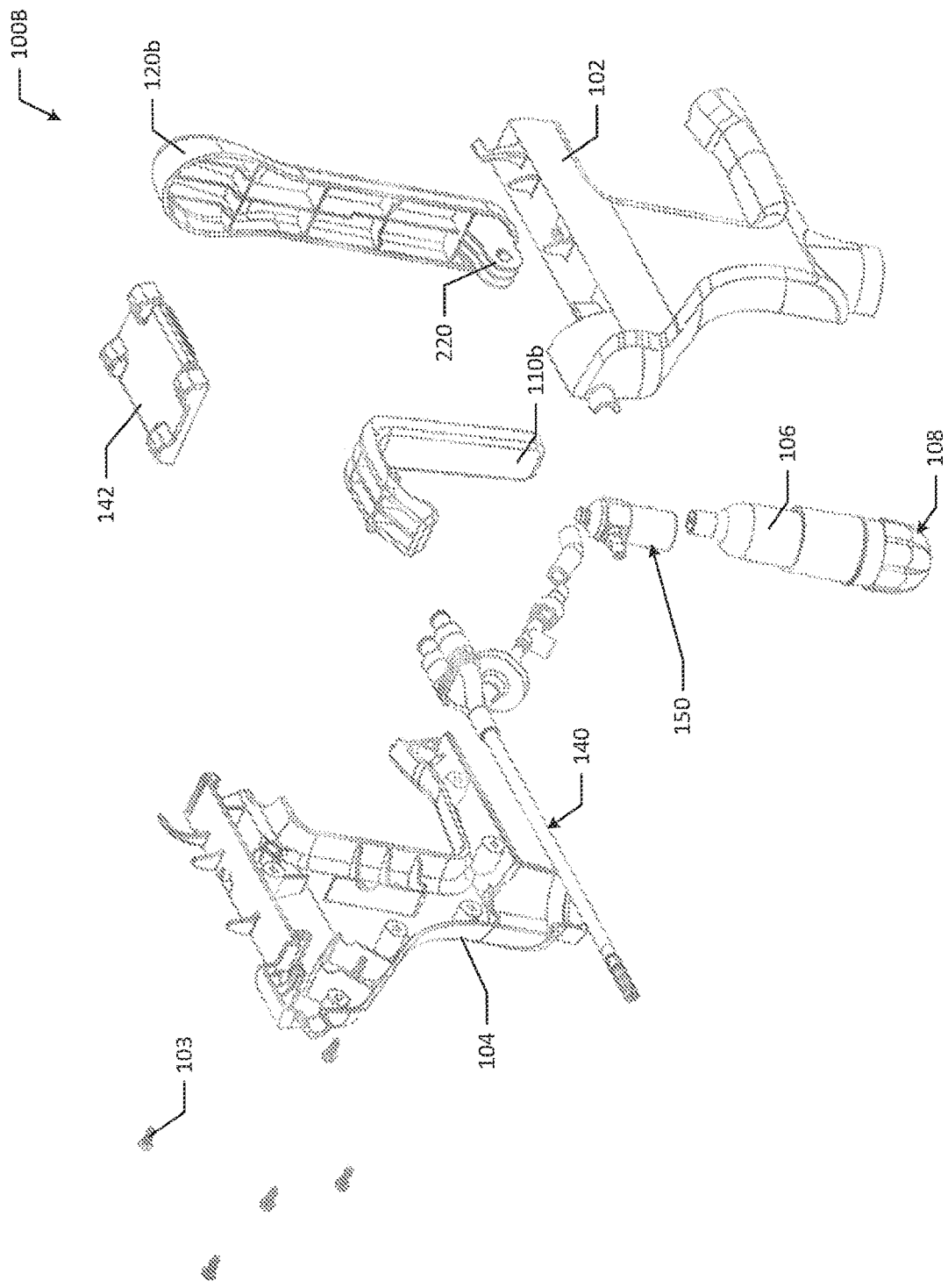
FIG. 2E is an exploded perspective view of the example handheld gas spray system of FIG. 2D.
Figure 2F:
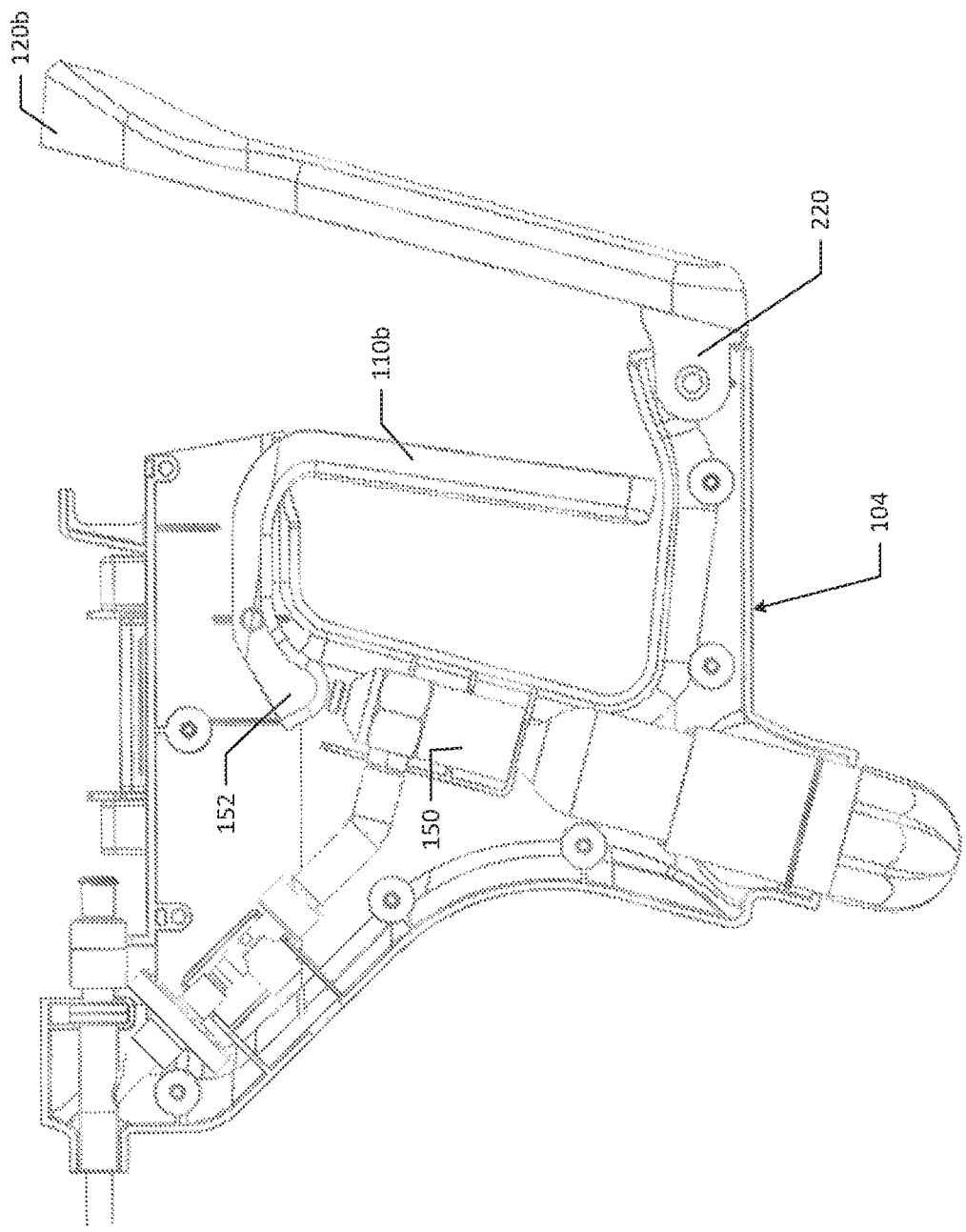
FIG. 2F is an elevated side view of a portion of the example handheld gas spray system of FIG. 2D

FIGS. 2D, 2E, 2F illustrate an alternative embodiment of the example handheld gas spray system 100B. In the illustrated example of FIGS. 2D, 2E, 2F, the handle 120b is connected to the housing 115 via a joint 220. The joint 220 enables the handle 120b to rotate about the joint 220 (instead of sliding as described for the embodiment of FIGS. 2A and 2B).

Gas Valve Assembly

Figure 3A:
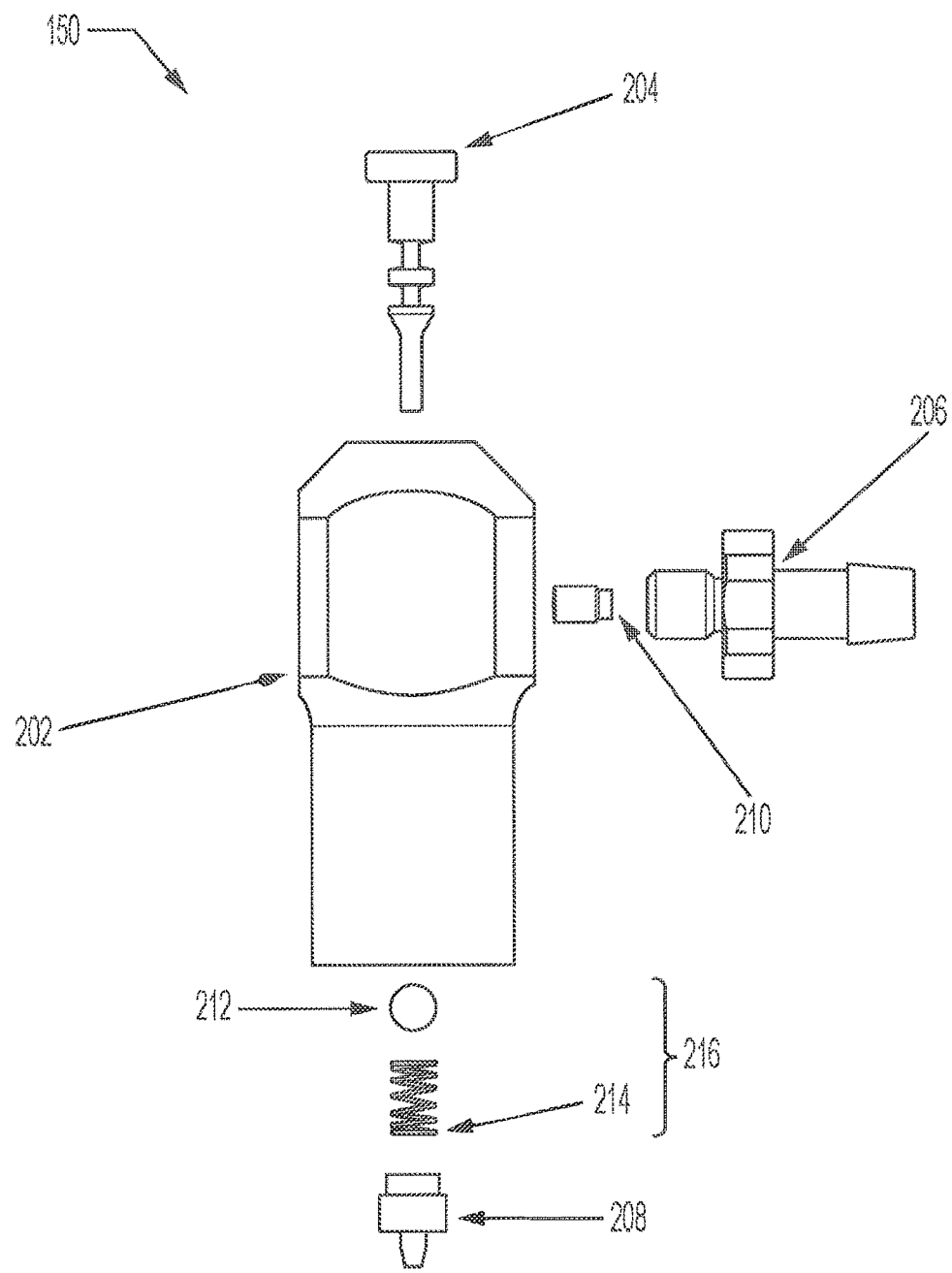
FIG. 3A is an exploded side view of an example gas valve assembly of the present disclosure.
Figure 3C:
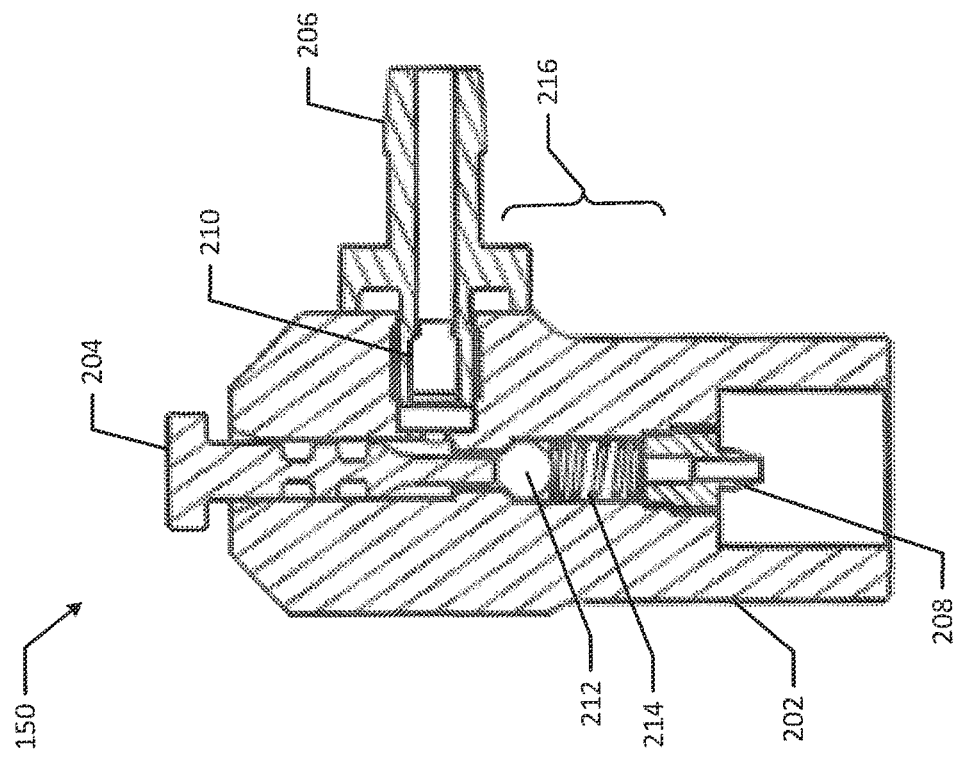
FIG. 3C is an elevated cross-sectional view taken along line 3C-3C of FIG. 3B.
Figure 3B:
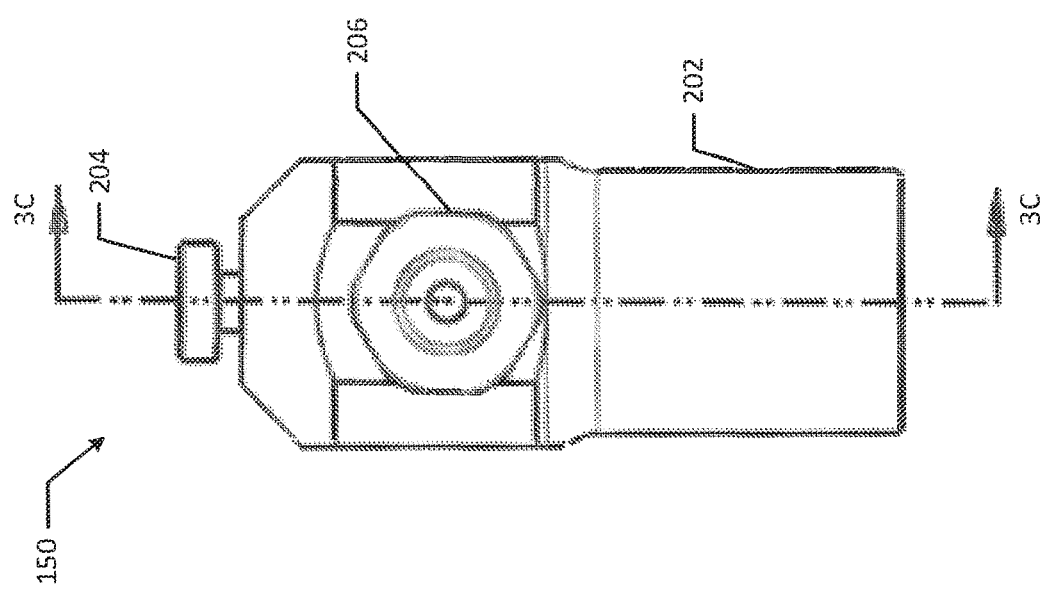
FIG. 3B is an elevated front view of the gas valve assembly of FIG. 3A.

FIGS. 3A, 3B and 3C illustrate the gas valve assembly 150. In the illustrated example, the gas valve assembly 150 includes a valve body 202 (a cross-sectional view of the valve body 202 is illustrated in FIG. 14C), a valve stem 204, a valve barb 206, and a puncture needle 208. A flow restrictor 210 is positioned between the valve body 202 and the valve barb 206. Additionally, the puncture needle 208 is connected to the valve body 202 with a ball 212 an spring 214.

The gas valve assembly 150 is adapted to controllably allow gas to flow from the gas cartridge 106 (e.g., a miniature compressed gas cartridge) to the fluid conveyance subassembly 140 of the device or system 100A, 100B. In an example, the puncture needle 208, which may also be referred to as a piercing needle, may be threaded into the valve body 202. Alternatively, the puncture needle 208 may be affixed to the valve body 202 using other attachment means (e.g., mechanical press fit, etc.). The puncture needle 208 is adapted to capture the spring 214 and ball 212 when threaded or otherwise installed into the valve body 202. Together, the ball 212 and spring 214 form a poppet 216. In an example, the lower portion of the valve body 202 is sized to threadingly engage with a threaded gas cartridge 106 (e.g., a threaded $CO_2$ cartridge). A cartridge sealing O-ring (not pictured) may be included to prevent leakage of gas during and after puncturing of the gas cartridge 106 by the puncture needle 208. An O-ring is provided as one example sealing structure, but it should be appreciated that any suitable elastomeric seal may be placed in this location that is sized to ensure that an adequate seal forms before the needle 208 punctures the pressurized gas cartridge 106, ensuring a leak-tight seal.

Additionally, a valve stem 204 is installed into the upper bore of the valve body 202. The valve stem 204 may include glands, which may have two stem O-rings (not pictured) installed thereon, which ensure the valve stem 204 is slidably connected to the valve body 202 without leaking. For example, the two stem O-rings provide a slidable and leak-tight connection between the valve stem 204 and the valve body 202. The gland dimensions, the O-ring sizing, and the bore sizing may be conventional for this type of articulating interface and should be apparent to those skilled in the art. It should be appreciated that less than or more than two sealing o-rings may be utilized to ensure a leaktight interface between the valve stem and valve body. The valve stem 204 is depressed to move the valve from its normally closed condition to its open state.

Figure 4A:
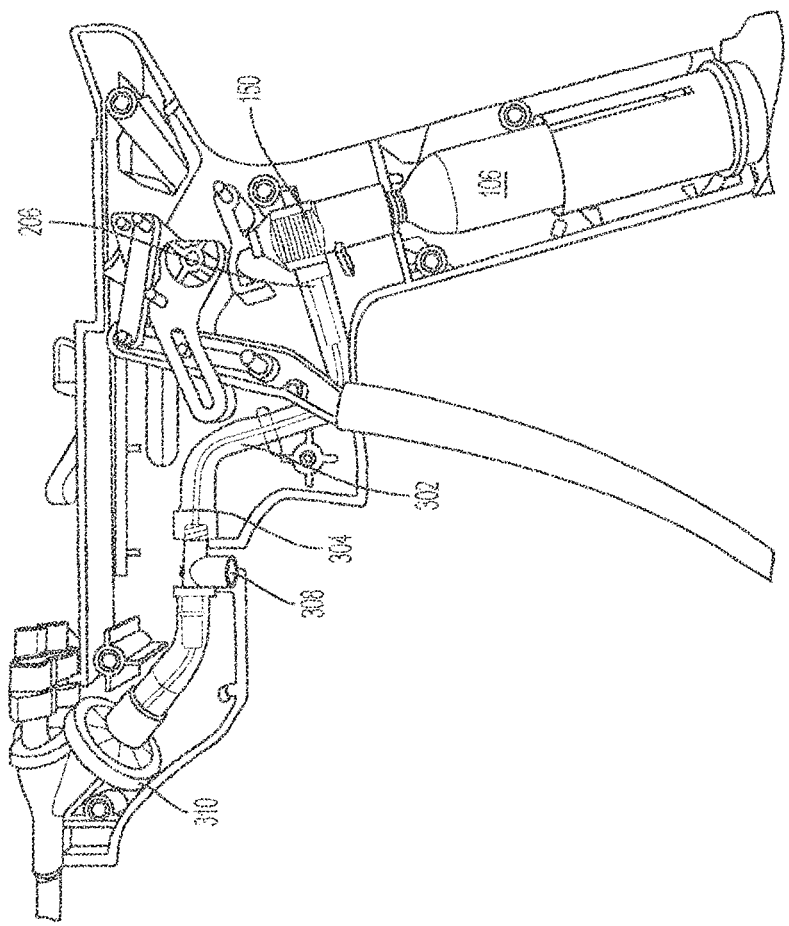
FIG. 4A is an elevated side view illustrating example gas tubing connections within an example handheld gas spray system according to the present disclosure.
Figure 4B:
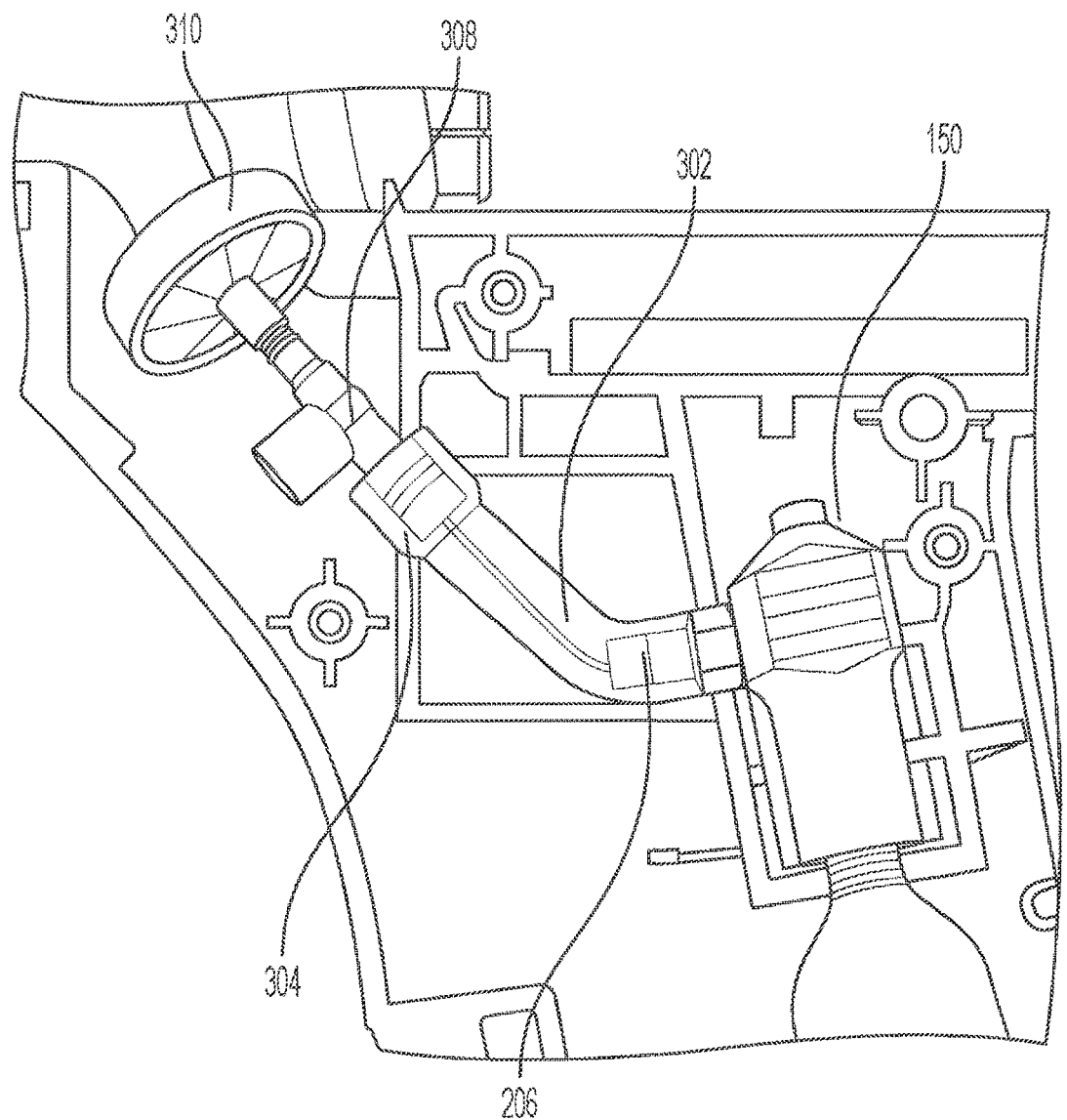
FIG. 4B is an elevated side view illustrating example gas tubing connections within an example handheld gas spray system according to the present disclosure.
Figure 4C:
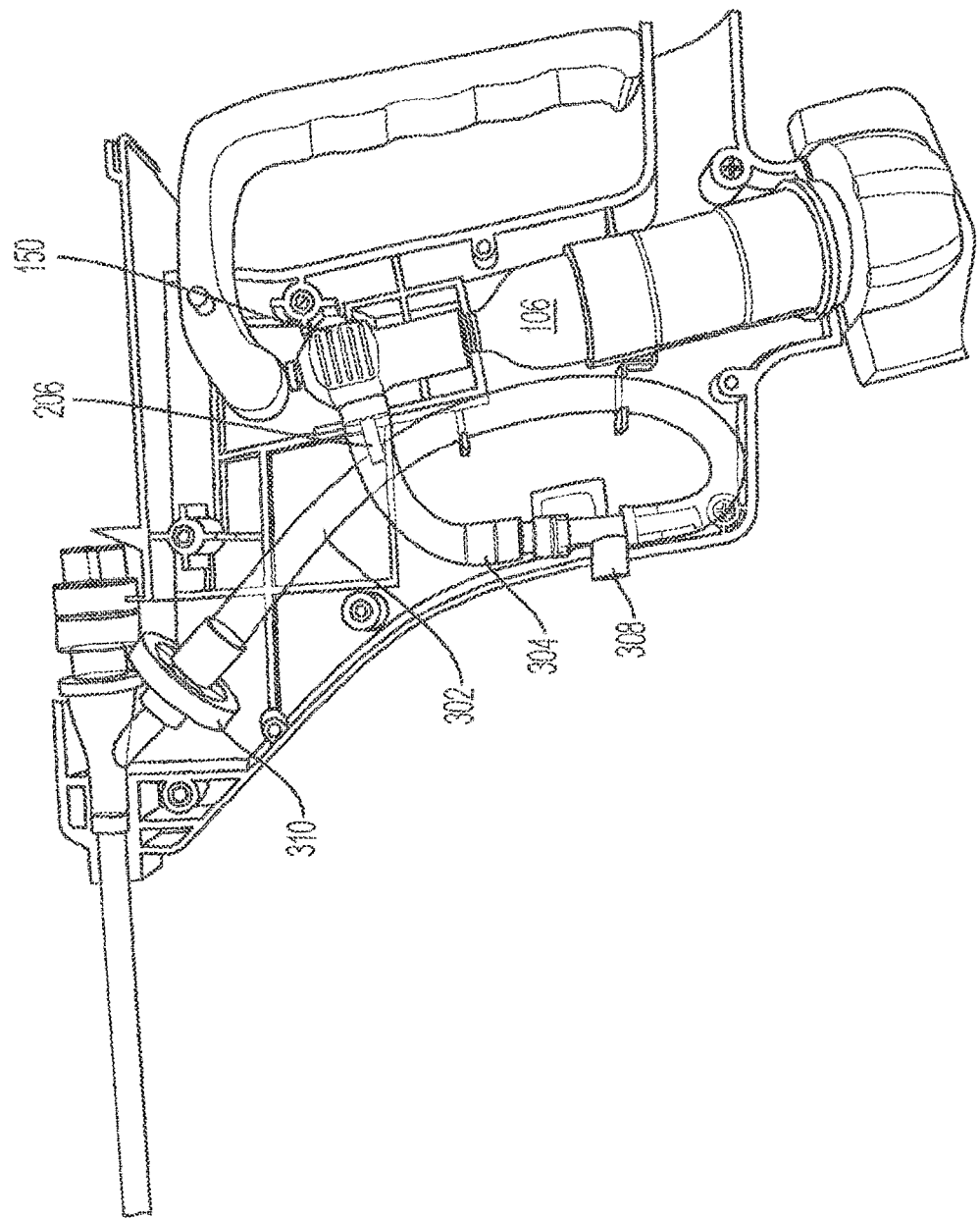
FIG. 4C is an elevated side view illustrating example gas tubing connections within an example handheld gas spray system according to the present disclosure.

The barb 206 may be installed via a captured O-ring seal or other O-ring type seal into a side port of the valve body 202 to convey gas into a gas tube (see gas tube 302 of FIGS. 4A, 4B and 4C). For example, the valve body 202 may feature a spotface (or other appropriately designed recess) on the surface coincident with a barb installation hole on the valve body 202 to ensure an adequate seal. Additionally, a flow restrictor 210 may be installed inside the barb 206 to control the flow of gas downstream, ensuring a safe and functionally useful flowrate. Critically, the flow restrictor 210 orifice is sized to ensure that choked flow results in a mass flowrate that is at all times consistent with values previously demonstrated at to be safe for use at a specified distance from patient tissue, considering the vapor pressure of the compressed fluid cartridge, e.g. a $CO_2$ cartridge.

FIGS. 4A, 4B and 4C illustrate the gas tubing connections between the gas cartridge 106 and gas valve assembly 150 to the fluid conveyance subassembly 140. FIG. 4A illustrates the gas tubing connections for system 100A while FIGS. 4B and 4C illustrate alternative examples of the gas tubing connections for system 100B. As illustrated in FIGS. 4A and 4B, the gas tube 302, which is connected to the valve barb 206 at a first end, leads to another barb 304 at a second end of the gas tube 302. The barb 204 may be Luer-connected to a relief valve 308. The relief valve 308 is provided to ensure that excess pressure is safely vented to the environment. For example, if the downstream portion of the device or system 100A, 100B become occluded when the gas flow is turned on, the relief valve 308 vents excess pressure to the environment.

In some examples, the relief valve 308 may be designed or specified by characterizing the normal operating pressure of the system 100A, 100B. For example, the minimum cracking pressure of such a relief valve 308 may be greater than or equal to the normal operating pressure of the section of the fluid path into which the relief valve 308 is installed. Additionally or alternatively, the maximum (cracking) pressure of the relief valve 308 may be characterized or selected based on an established safety limit (e.g., a clinically-determined maximum safe operating pressure). For example, to determine the maximum pressure threshold, a range of pressures exceeding the normal operating pressure of the compressed gas cartridge 106 may be supplied to the gas valve assembly 150 and the resulting impact pressure at a given distance from the device spray tip may then be observed or measured. More generally, the relief valve 308 may be sized to ensure relief of system pressure in instances where pressure in the upstream system would result in excess pressure applied to the tissue at a given distance away from the spray tip. In one example, the cracking pressure may be specified in a range between approximately 70 to 110 kilopascals (kPa) differential pressure.

Additionally, the relief valve 308 may be connected via a Luer slip connection to a gas filter 310. In some examples, the gas filter 310 may be intended to ensure the gas is sterile and essentially free of particulate matter before delivery to the patient. The gas filter 310 may comprise an appropriate membrane material selected based on the desired composition of sealant and gas. For example, if the compressed gas is carbon dioxide and the sealant composition is aqueous, the gas filter 310 may be implemented to contain a hydrophobic membrane material (e.g., PTFE) to ensure that wetting does prevent or limit or reduce the passage of gas flow.

Fluid Conveyance Sub-Assembly

The fluid conveyance subassembly 140 facilitates the transport of the two surgical sealant components from syringe 130 and a gas stream from the device handle 120 to the distal tip. Until reaching the spray tip 414 subassembly, these three fluid streams are not in fluid communication. This is of importance to the functionality of systems 100A, 100B because polymerization of the two-component sealant begins rapidly after the two components of the two-component sealant meet one another. It is desirable to deliver a spray of well-mixed, but not polymerized, sealant to the target tissue site.

Figure 5A:
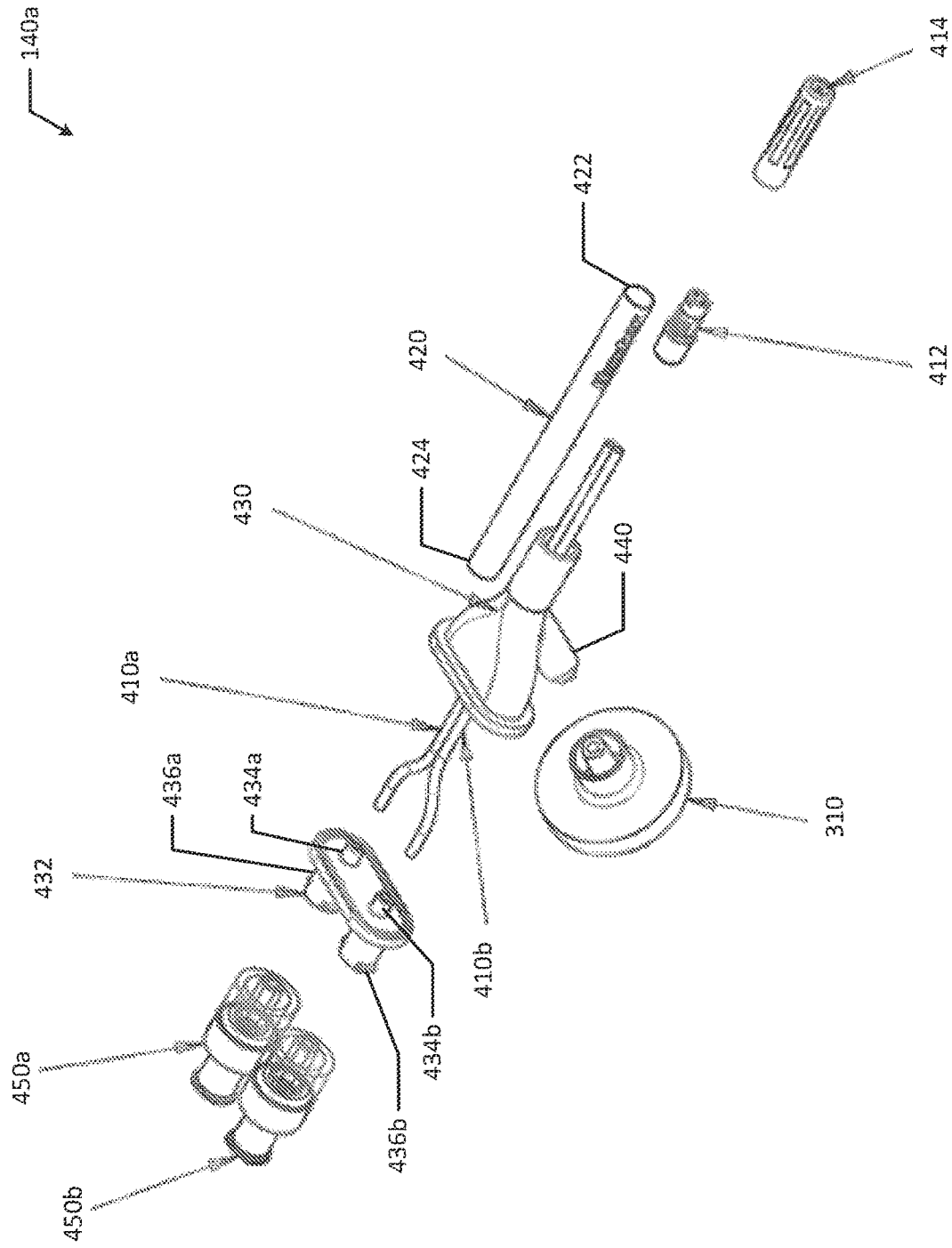
FIG. 5A is an exploded perspective view of an example fluid conveyance subassembly according to the present disclosure.
Figure 5B:
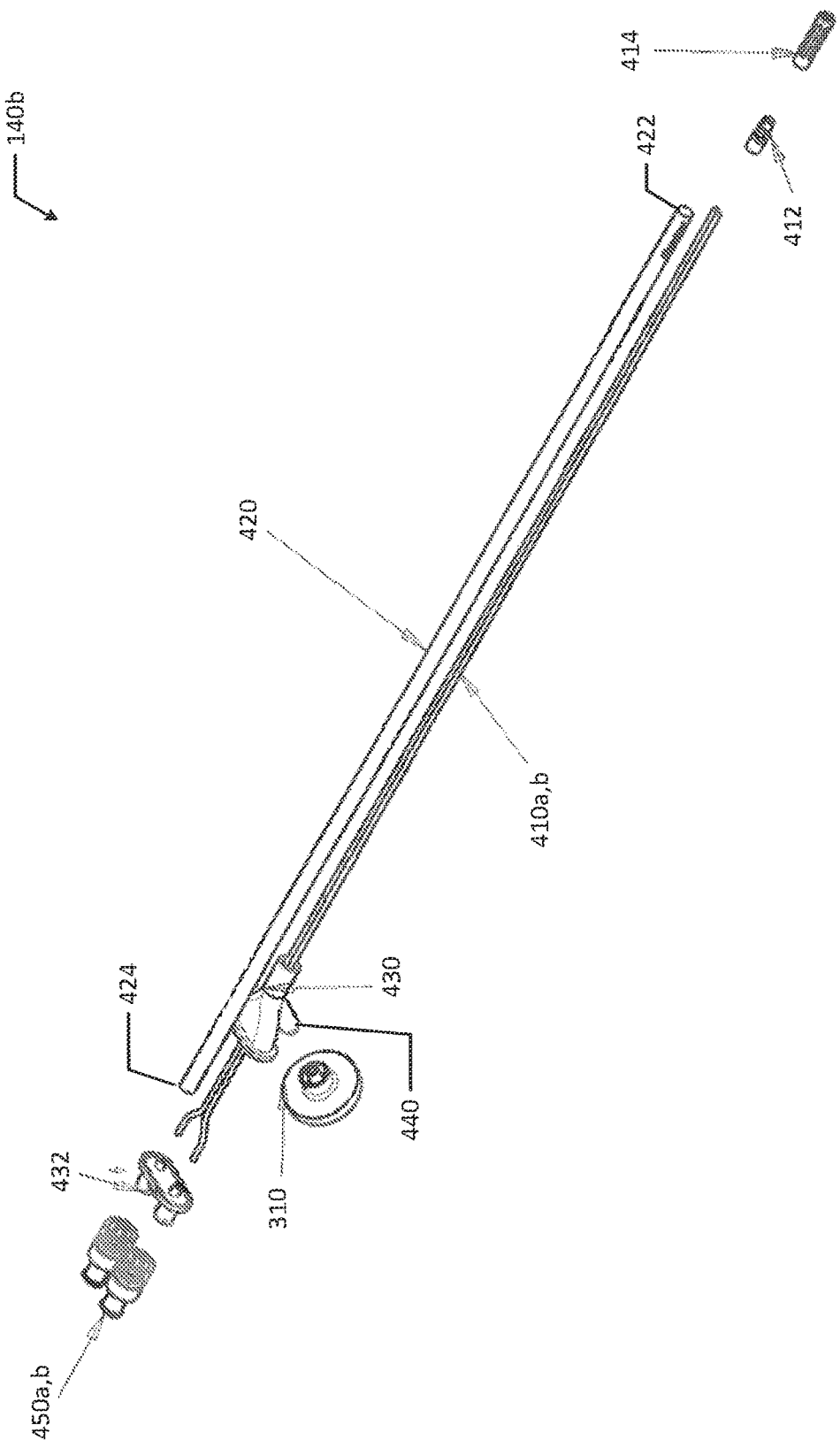
FIG. 5B is an exploded perspective view of an example fluid conveyance subassembly according to the present disclosure.
Figure 5C:
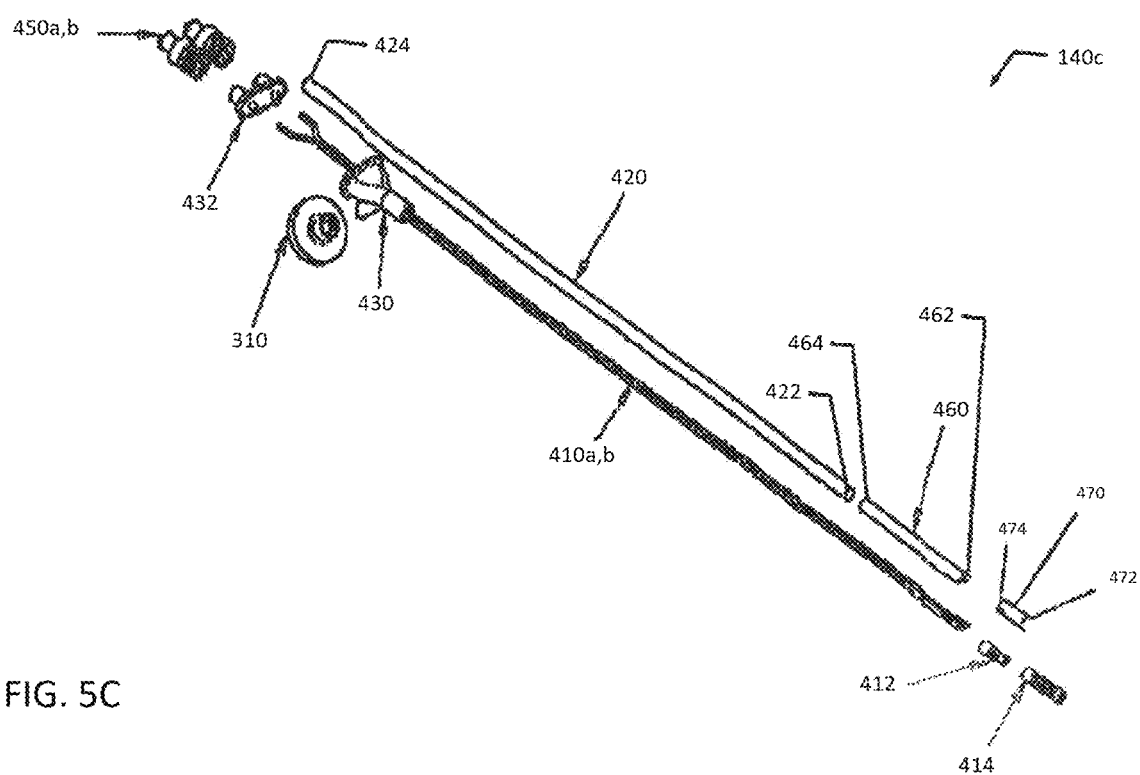
FIG. 5C is an exploded perspective view of an example fluid conveyance subassembly according to the present disclosure.

The fluid conveyance subassembly 140 may have various configurations, three of which are illustrated in FIGS. 5A, 5B and 5C. FIG. 5A illustrates a first configuration of the fluid conveyance subassembly 140a that is adapted for open surgery. In an example, the fluid conveyance subassembly 140a may have an approximate working length of 6 cm and may generally comprise a rigid construction. As illustrated in FIG. 5A, the fluid conveyance subassembly 140a includes sealant tubes 410a,b that are routed down the length of the outer cannula 420 to the threaded plug 412. At the outer cannula's 420 distal end 422, the outer cannula 420 may be bonded to the threaded plug 412 providing a gastight or leak-tight seal. The threaded plug 412 may be coupled to a spray tip 414 subassembly (e.g., threadingly coupled). At the outer cannula's 420 proximal end 424, the outer cannula 420 may be bonded to a Y-connector distal component 430 providing a gastight or leak-tight seal between the outer cannula 420 and the Y-connector distal component 430 (additional views of the Y-connector distal component 430 are illustrated in FIGS. 14E and 14F).

Figure 14D:
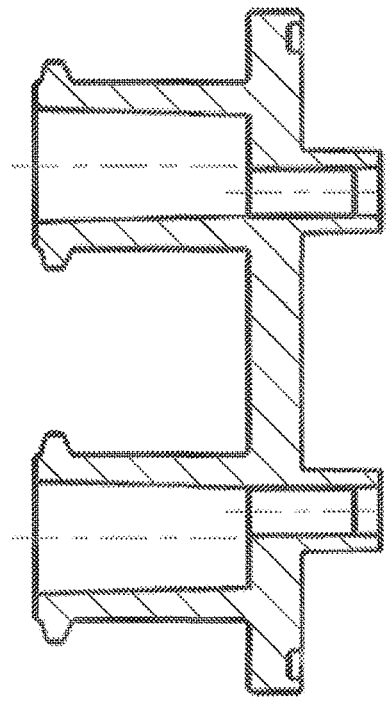
Figure 14A:
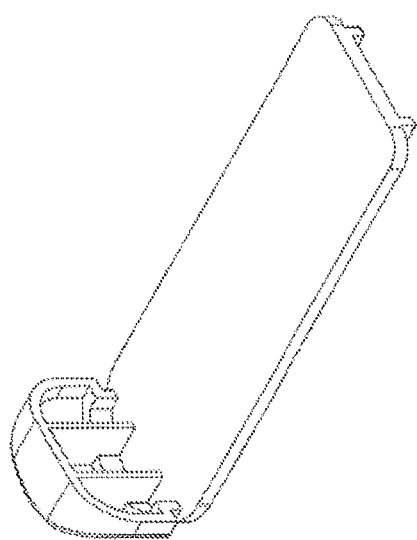
Figure 14C:
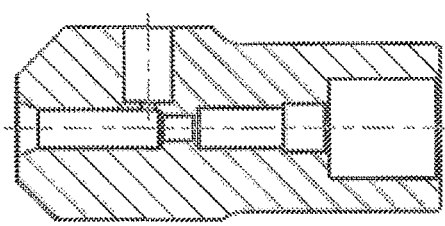
Figure 14F:
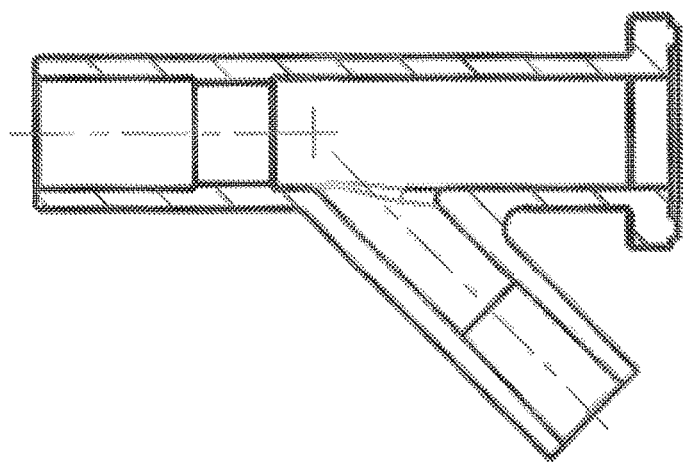
Figure 14E:
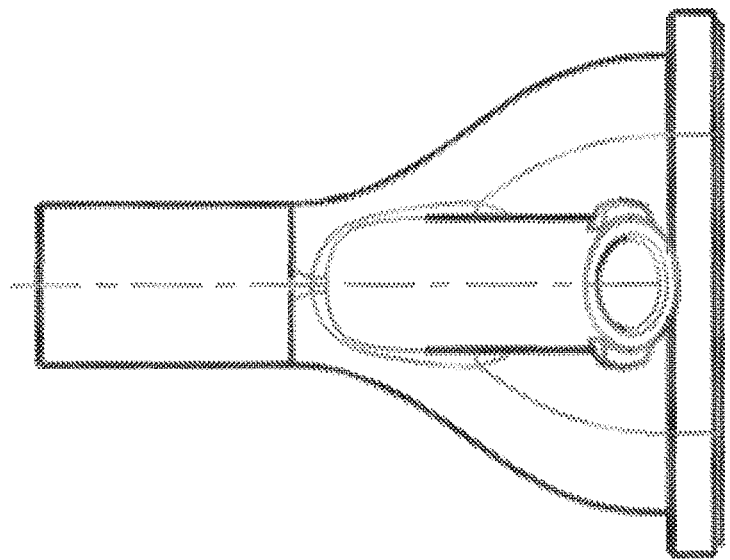

A Y-connector proximal component 432 may be ultrasonically welded to the Y-connector distal component 430 (a cross-sectional view of the Y-connector proximal component 432 is illustrated in FIG. 14D). In an example, the sealant tubes 410a and 410b, hereinafter referred to generally as sealant tube(s) 410, are bonded within two bosses 434a,b located on the Y-connector proximal component 432. The other ends of the sealant tubes 410 are bonded to corresponding receiving structures (described in more detail below) in the threaded plug 412. A gas connection port 440 may be provided on an underside of the Y-connector distal component 430, allowing connection to the gas filter 310 described in FIGS. 4A and 4B. The gas filter 310 may connect to the gas connection port 440 via a Luer lock connection. The fluid conveyance subassembly 140a may also include check valves 450a and 450b, which may be installed onto corresponding female Luer lock connections 436a,b of the Y-connector proximal component 432 to prevent backflow into the syringe 130 under pressure. It should be noted that the female Luer connections 436a,b of the Y-connector proximal component 432 may be positioned with a predetermined axial offset corresponding to the outlet spacing of the syringe 130 to be used.

FIG. 5B illustrates a second configuration of the fluid conveyance subassembly 140b that is adapted for laparoscopic surgery. For example, laparoscopic surgical procedures may require a longer cannula 420 as illustrated in FIGS. 5B and 5C while procedures closer to the surface of the skin may use a shorter cannula 420 as illustrated in FIG. 5A. In an example, the fluid conveyance subassembly 140b may have an approximate working length of 40 cm and may generally comprise a rigid construction. As illustrated in FIG. 5B, the fluid conveyance subassembly 140b includes each of the components described above in subassembly 140a. However, the sealant tubes 410a,b and the outer cannula 420 are longer, such that the fluid conveyance subassembly 140b has a longer working length.

FIG. 5C illustrates a third configuration of the fluid conveyance subassembly 140c that is adapted for laparoscopic surgery. In an example, the fluid conveyance subassembly 140c may have an approximate working length of 40 cm and may generally comprise a rigid construction with a malleable section allowing the device to bend at its distal end for positionability during laparoscopic surgery. As illustrated in FIG. 5C, the fluid conveyance subassembly 140c includes each of the components described above in subassembly 140a and 140b. However, the sealant tubes 410a,b and the outer cannula 420 are longer, similar to fluid conveyance subassembly 140b, such that the fluid conveyance subassembly 140c has a longer working length. Additionally, the fluid conveyance subassembly 140c includes an additional malleable tube 460 and malleable collar 470 positioned between outer cannula 420 and thread plug 412. For example, instead of the outer cannula's 420 distal end 422 being bonded to the thread plug, as in FIG. 5A, the outer cannula's 420 distal end 422 may be coupled or bonded to malleable tube 460, which is coupled or bonded to collar 470. For example, a proximal end 464 of the malleable tube 460 may be connected to the distal end 422 of the outer cannula 420 and a distal end 462 of the malleable tube 460 may be connected to a proximal end 474 of the collar 470. Additionally, a distal end 472 of the collar 470 may be connected to the thread plug 412. The collar 470 may be bonded to the threaded plug 412 providing a gastight or leak-tight seal. Similar to subassembly 140a and 140b, the threaded plug 412 may be coupled to a spray tip 414 subassembly.

The entire malleable section (e.g., malleable tube 460 and collar 470) may be approximately 4.5 cm in length and therefore the outer cannula 420 is shortened relative to the sealant tubes 410a,b compared to fluid conveyance subassembly 140b. Referring back to FIG. 5B, the sealant tubes 410a,b hereinafter sealant tube(s) 410 may be approximately the same length as the combined length of the Y-connector distal component 430 and outer cannula 420. However, the sealant tubes 410 of FIG. 5C may be approximately the same length as the combined length of the Y-connector distal component 430, outer cannula 420, malleable tube 460 and collar 470.

In each of FIGS. 5A, 5B and 5C, the first and second sealant tube(s) 410 provide fluid communication between fluid containers, such as syringe 130 and ultimately the spray tip 414 subassembly. The fluids travel, while separated, and exit the syringe 130, passing check valves 450 before entering the Y-connector proximal component 432 and passing through the sealant tubes 410. The fluids stay completely separated as they travel through the system up to the threaded plug 412. Then the fluids travel into the detachable spray tip sub-assembly 414, which may be removably coupled to the threaded plug 412. While the systems 100A, 100B are shown with interfaces for receiving two sources of fluid, it should be appreciated that systems 100A, 100B may be configured to receive more than two sources of fluid (e.g., sealant). For example, systems 100A, 100B may be configured to mix and dispense an adhesive or sealant, such as a biological sealant that is made up of three or more component fluids. It should also be appreciated that the systems 100A, 100B may include additional interfaces (e.g., syringe interfaces) for additional fluid containers. For example, the systems 100A, 100B illustrated herein show a dual component syringe 120 with two discrete sealant tubes 410, however, three or more fluid containers and/or sealant tubes 410 may be used. For example, some multi-component fluids may include three or more fluids that are mixed to form a sealant or adhesive. Additionally, it should be appreciated that systems 100A, 100B may be configured to receive a single source of fluid (e.g., one-component sealant). For example, systems 100A, 100B may be configured to dispense a one-component adhesive. It should be appreciated that the systems 100A, 100B may include a single interface for a single fluid container. For example, the systems 100A, 100B illustrated herein show a dual component syringe 120 with two discrete sealant tubes 410, however, one single fluid container and/or sealant tube 410 may be used.

Outer Cannula, Malleable Tube, Collar, and Sealant Tubes

Figure 6A:
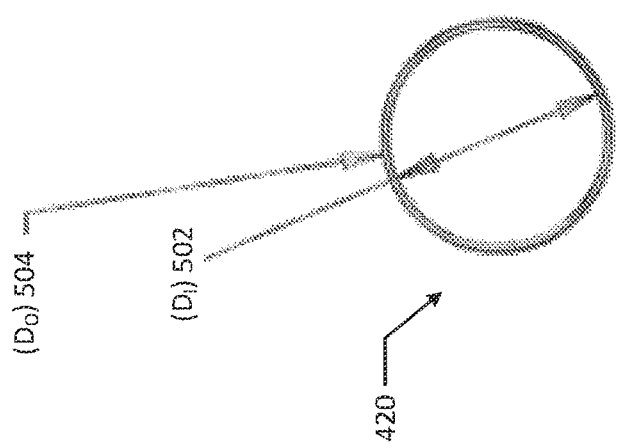
FIG. 6A is an elevated front view of an example outer cannula according to the present disclosure.
Figure 6B:
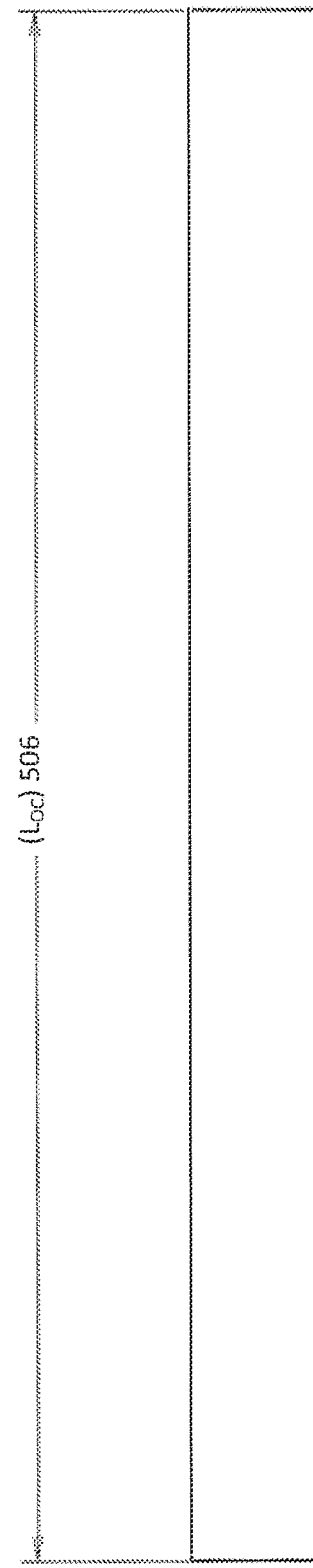
FIG. 6B is an elevated side view of an example outer cannula according to the present disclosure.

FIGS. 6A and 6B illustrate end and side profiles of the outer cannula 420. The outer cannula 420 may have an inside diameter ($D_I$) 502, an outside diameter ($D_O$) 504, and a length ($L_{OC}$) 506. The inside diameter ($D_I$) 502 may be approximately 5 mm and the outside diameter ($D_O$) 504 may be approximately 5.30 mm. The length ($L_{OC}$) 506 may vary depending on the configuration of the fluid conveyance subassembly 140. For example, the length ($L_{OC}$) 506 may be approximately 63 mm, 401 mm and 342 mm for subassemblies 140a, 140b and 140c respectively. In an example, the outer cannula 420 may be made from a rigid material, such as 304 stainless steel.

Figure 7A:
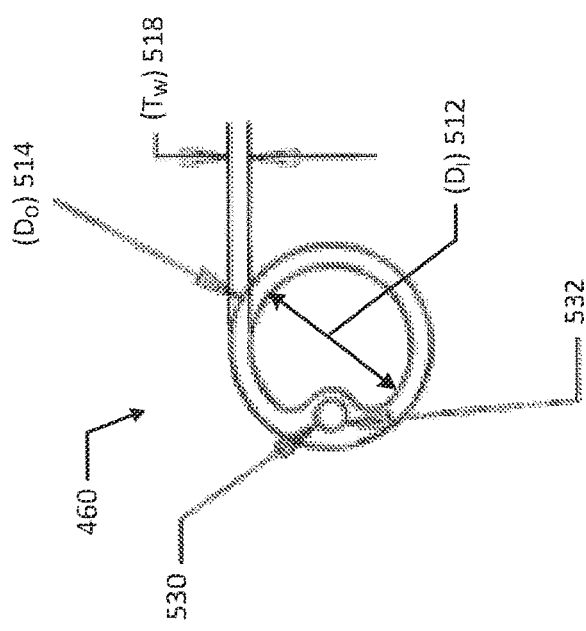
FIG. 7A is an elevated front view of an example malleable tube according to the present disclosure.
Figure 7B:
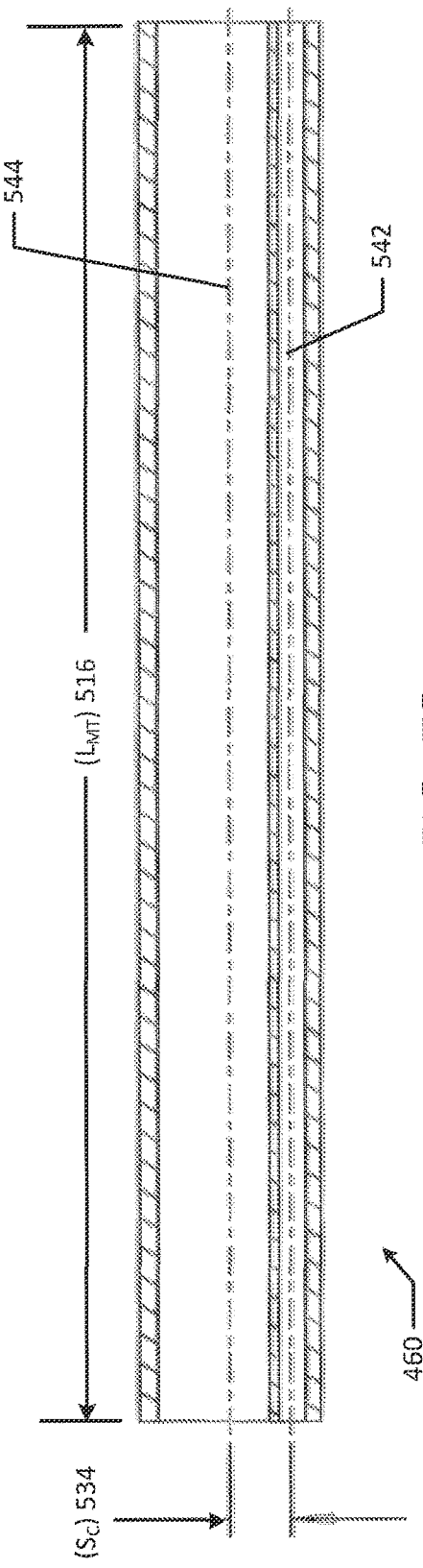
FIG. 7B is an elevated side view of an example malleable tube according to the present disclosure.

FIGS. 7A and 7B illustrate an end and cross-sectional profile of the malleable tube 460. The malleable tube 460 may have an inside diameter ($D_I$) 512, an outside diameter ($D_O$) 514, a length ($L_{MT}$) 516, and wall thickness ($T_W$) 518. The inside diameter ($D_I$) 512 may be approximately 4 mm and the outside diameter ($D_O$) 514 may be approximately 5 mm. The length ($L_{MT}$) 516 may be approximately 65 mm. The wall thickness ($T_W$) 518 of the malleable tube 460 may be approximately 0.5 mm. Additionally, the malleable tube 460 may include an aperture or channel 530 extending the length of the malleable tube 460 that is sized and shaped to receive a wire 532. The channel 530 may have a diameter of approximately 0.75 mm. The spacing ($S_C$) 534 between a longitudinal axis 542 of channel 530 and a longitudinal axis 544 of tube 460 may be approximately 1.7 mm.

The wire 532 may be a stiffening wire to add additional strength and support to the malleable tube 460. Additionally, the wire 532 may be adapted to provide malleability to tube 460 while retaining the shape of the malleable tube 460. The wire 532 may be a malleable wire and may be made of stainless steel. The malleable tube 460 may be made of a malleable plastic or rubber material. In an example, the malleable tube 460 is made of thermoplastic polyurethane elastomer.

Figure 8B:
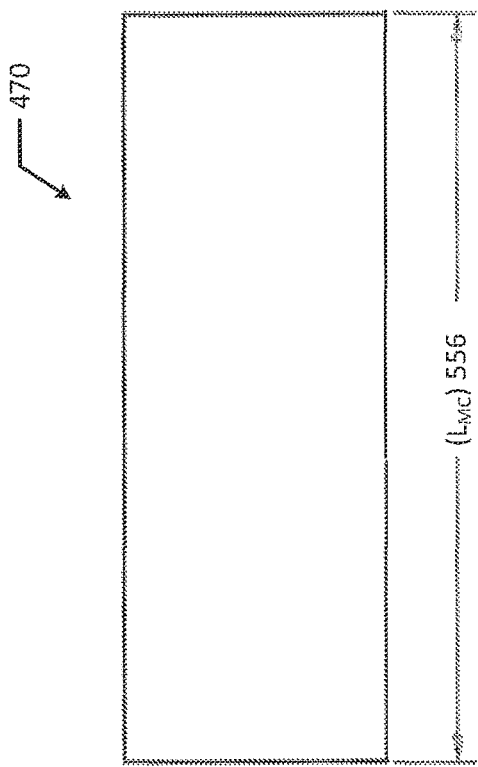
FIG. 8B is an elevated side view of an example malleable collar according to the present disclosure.
Figure 8A:
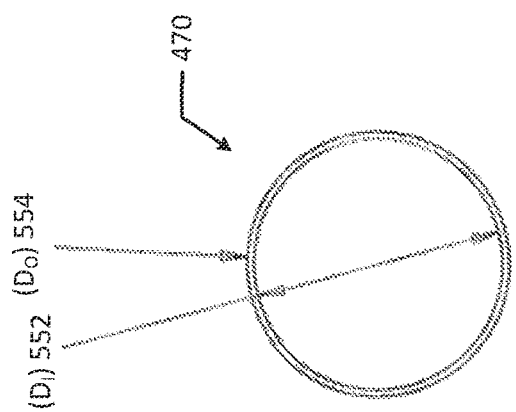
FIG. 8A is an elevated front view of an example malleable collar according to the present disclosure.

FIGS. 8A and 8B illustrate end and side profiles of the collar 470. The collar 470 may have an inside diameter ($D_I$) 552, an outside diameter ($D_O$) 554, and a length ($L_{MC}$) 556. The inside diameter ($D_I$) 552 may be approximately 5 mm and the outside diameter ($D_O$) 554 may be approximately 5.30 mm. The length ($L_{MC}$) 556 may be approximately 15 mm. In an example, the collar 470 may be made from a rigid material, such as 304 stainless steel. In another example, the collar 470 may be made of a rigid or semi-rigid plastic material. Alternatively, the collar 470 may be made of a plastic or elastomeric material similar to malleable tube 460. Alternatively, the collar 470 may be integrated as part of threaded plug 412.

FIGS. 9A and 9B illustrate end and side profiles of a sealant tube 410. The sealant tube 410 may have an inside diameter ($D_I$) 562, an outside diameter ($D_O$) 564, and a length ($L_{ST}$) 566. The inside diameter ($D_I$) 562 may be approximately 1 mm and the outside diameter ($D_O$) 564 may be approximately 1.78 mm. The length ($L_{ST}$) 566 may vary depending on the configuration of the fluid conveyance subassembly 140. For example, the length ($L_{ST}$) 566 may be approximately 93 mm, 432 mm and 432 mm for subassemblies 140a, 140b and 140c respectively. In an example, the sealant tube 410 may be made from an elastic polymer, such as ethylene-vinyl acetate ("EVA").

Threaded Plug

FIGS. 13A-G illustrate an example embodiment of threaded plug 412. As discussed above, the fluid conveyance subassembly 140a includes sealant tubes 410a,b that are routed down the length of the outer cannula 420 to the threaded plug 412. In an example, the outer cannula 420 (or malleable collar 470) may be bonded to the threaded plug 412 providing a gastight or leak-tight seal. The threaded plug 412 may be coupled to a spray tip subassembly 414. For example, the threaded plug 412 may include external threads 902 that are adapted to engage corresponding threads (e.g., threaded portion 636 of tip body 610).

Figure 13B:
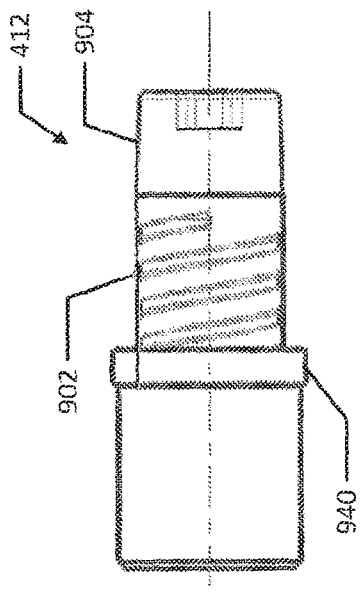
FIG. 13B is an elevated side view of an example threaded plug according to the present disclosure.
Figure 13A:
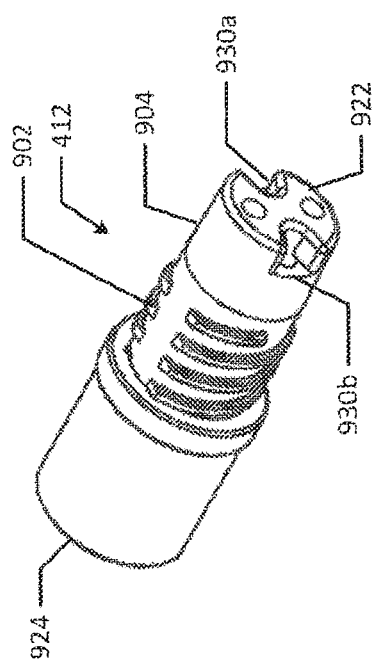
FIG. 13A is a perspective view of an example threaded plug according to the present disclosure.
Figure 13D:
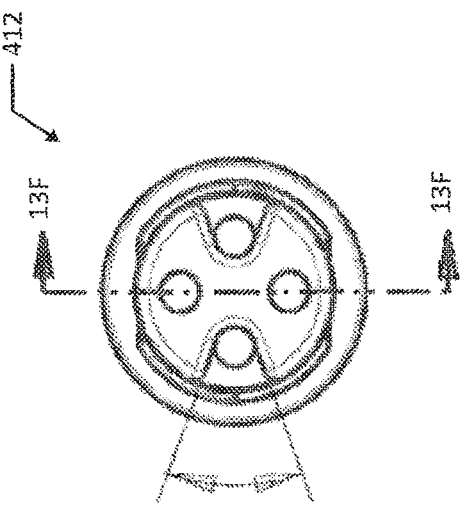
FIG. 13D is an elevated front view of an example threaded plug according to the present disclosure.
Figure 13C:
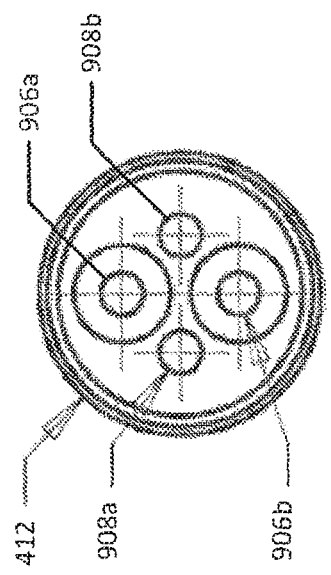
FIG. 13C is an elevated back view of an example threaded plug according to the present disclosure.
Figure 13E:
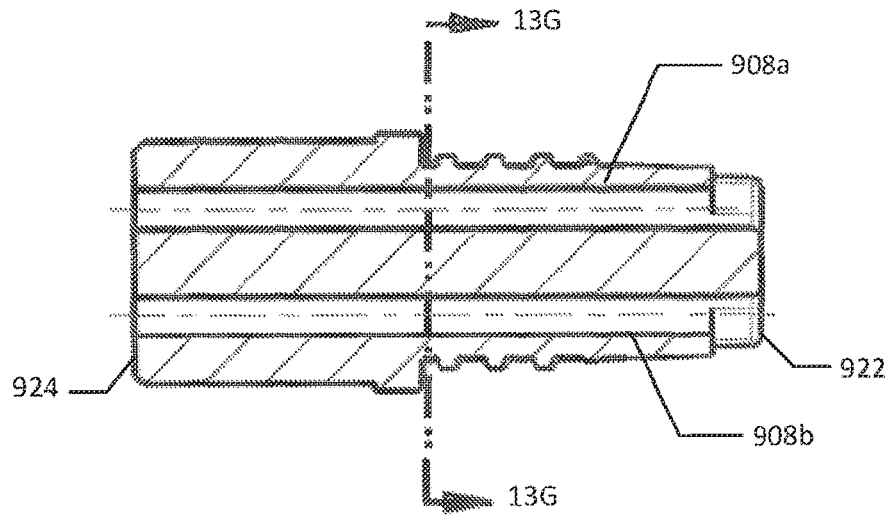
FIG. 13E is an elevated cross-sectional view of an example threaded plug according to the present disclosure.
Figure 13F:
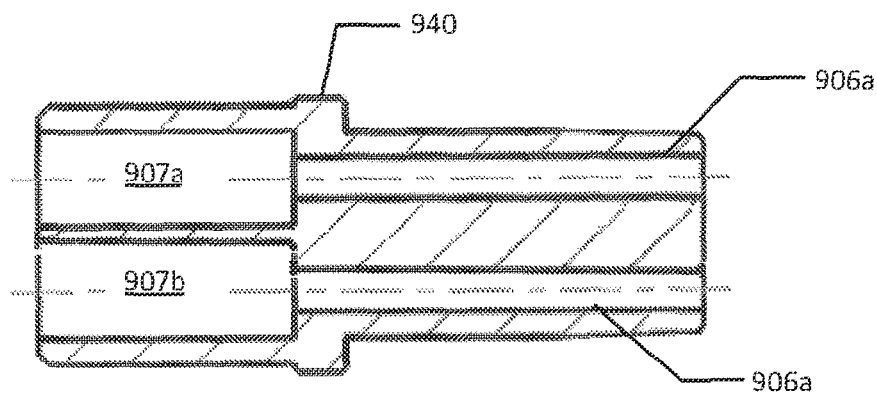
FIG. 13F is an elevated cross-sectional view taken along line 13F-13F of FIG. 13D.
Figure 13G:
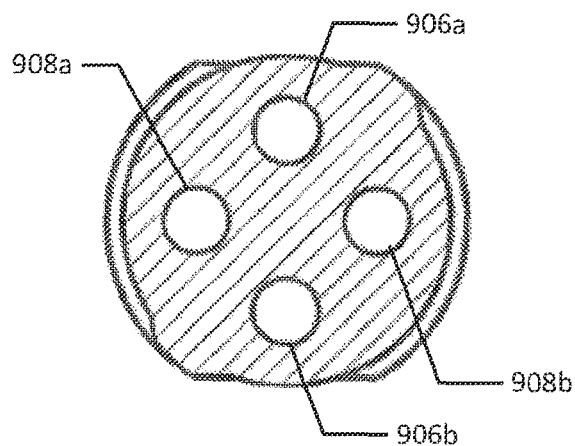
FIG. 13G is an elevated cross-sectional view taken along line 13G-13G of FIG. 13E.

The threaded plug 412 facilitates removable connection of the spray tip subassembly 414 to the outer cannula 420 or the malleable collar 470 depending on the configuration of the fluid conveyance subassembly 140. By design, the threaded plug 412 features a taper (e.g., tapered surface 904) to seal against an inner surface of the spray tip body 610, preventing leakage of the pressurized fluid mixture. Additionally, the threaded plug 412 may include two sealant passageways 906a,b (hereinafter referred to generally as sealant passageways 906) that are adapted to receive the corresponding sealant tubes 410a,b at a proximal end 924 of the threaded plug 412. For example, as illustrated in FIG. 13F, the sealant passageways 906a,b may include sealant tube accepting portions 907a,b that are sized and shaped such that a corresponding sealant tube 410 may be press-fit into threaded plug 412 and/or bonded within the accepting portion 907 of threaded plug 412 to form a fluid-tight seal.

The threaded plug 412 also includes one or more gas passageways 908a,b (hereinafter referred to generally as gas passageways 908) that are adapted to allow passage of the gas from the outer cannula 420 to the spray tip subassembly 414. The gas passageways 908a,b and the sealant passageways 906a,b extend from the proximal end 924 to the distal end 922 of the threaded plug. At the distal end 922 of the plug 412, the gas passageways 908 may be configured to open to the spray tip subassembly 414 before the sealant passageways 906, thereby allowing the gas to adequately spread through the spray tip before the sealant enters the spray tip, which may assist with properly mixing and atomizing the two component sealant. For example, as illustrated in FIG. 13A, the plug 412 may include two recesses 930a,b that allow the gas to communicate with the spray tip subassembly 414 prior to the sealant communicating with and entering the spray tip. In an example, each of the sealant passageways 906 and gas passageways 908 may have a diameter of approximately 0.8 mm.

The threaded plug may also include a flange 940 that is configured to serve as a stopper and abut the outer cannula 420 when the threaded plug 412 is coupled to the cannula 420 (or similarly the malleable collar depending on the configuration).

As sealants travel down sealant tubes 410a,b and gas flows through outer cannula 420, the fluids stay completely separated as they travel through the system and remain separated as the sealants travel through sealant passageways 906 and as the gas travels through gas passageways 908 of the threaded plug 412. Specifically, the sealant tubes 410 and plug 412 ensure that the fluids remain isolated as they travel between the syringe 130 and the spray tip subassembly 414. Then the fluids (e.g., sealant components and gas) travel into the detachable spray tip sub-assembly 414, which may be coupled to the threaded plug 412, where the fluids start to mix.

Spray Tip Sub-Assembly

Figure 10A:
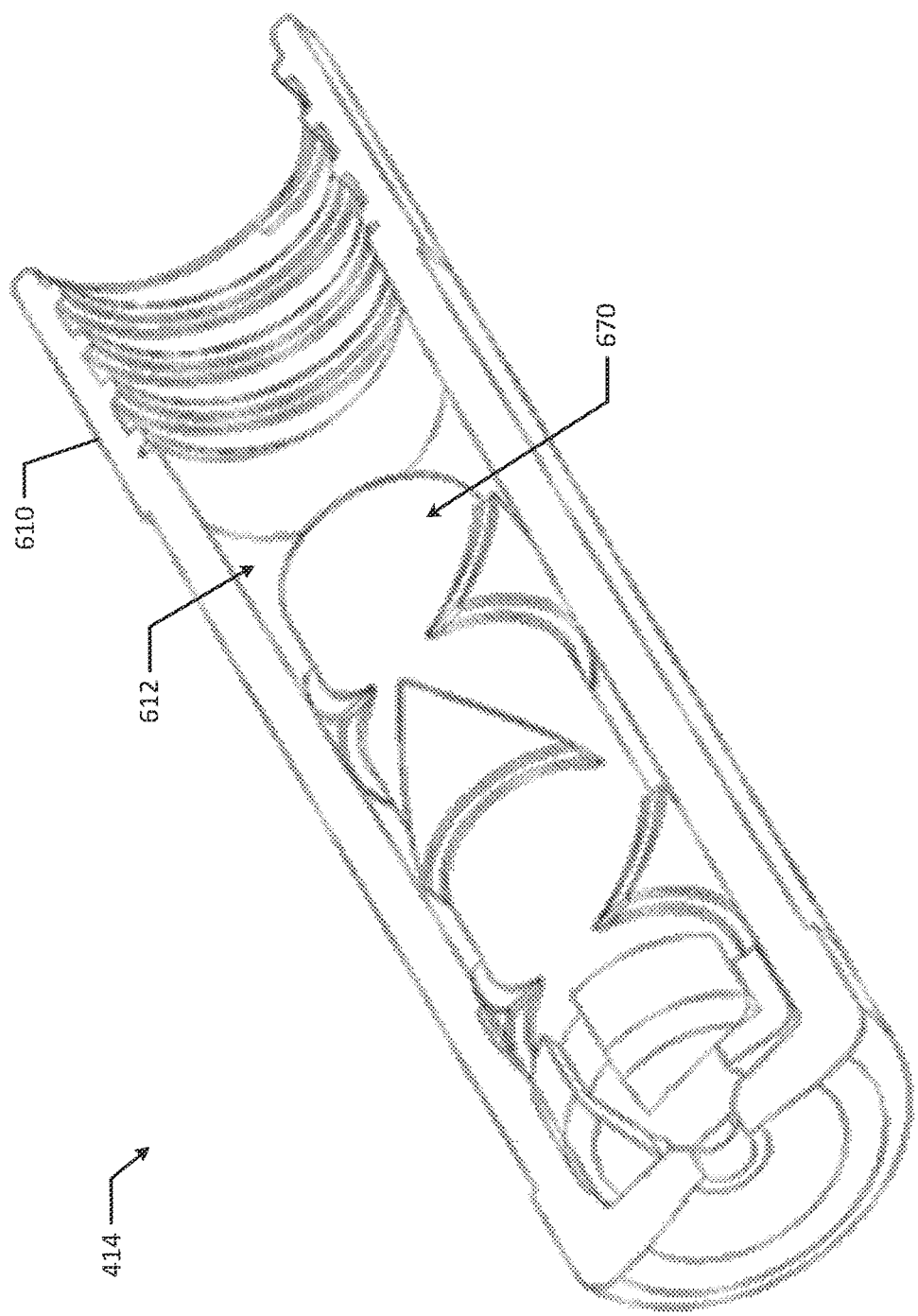
FIG. 10A is perspective cross-sectional view of an example spray tip subassembly according to the present disclosure.
Figure 10B:
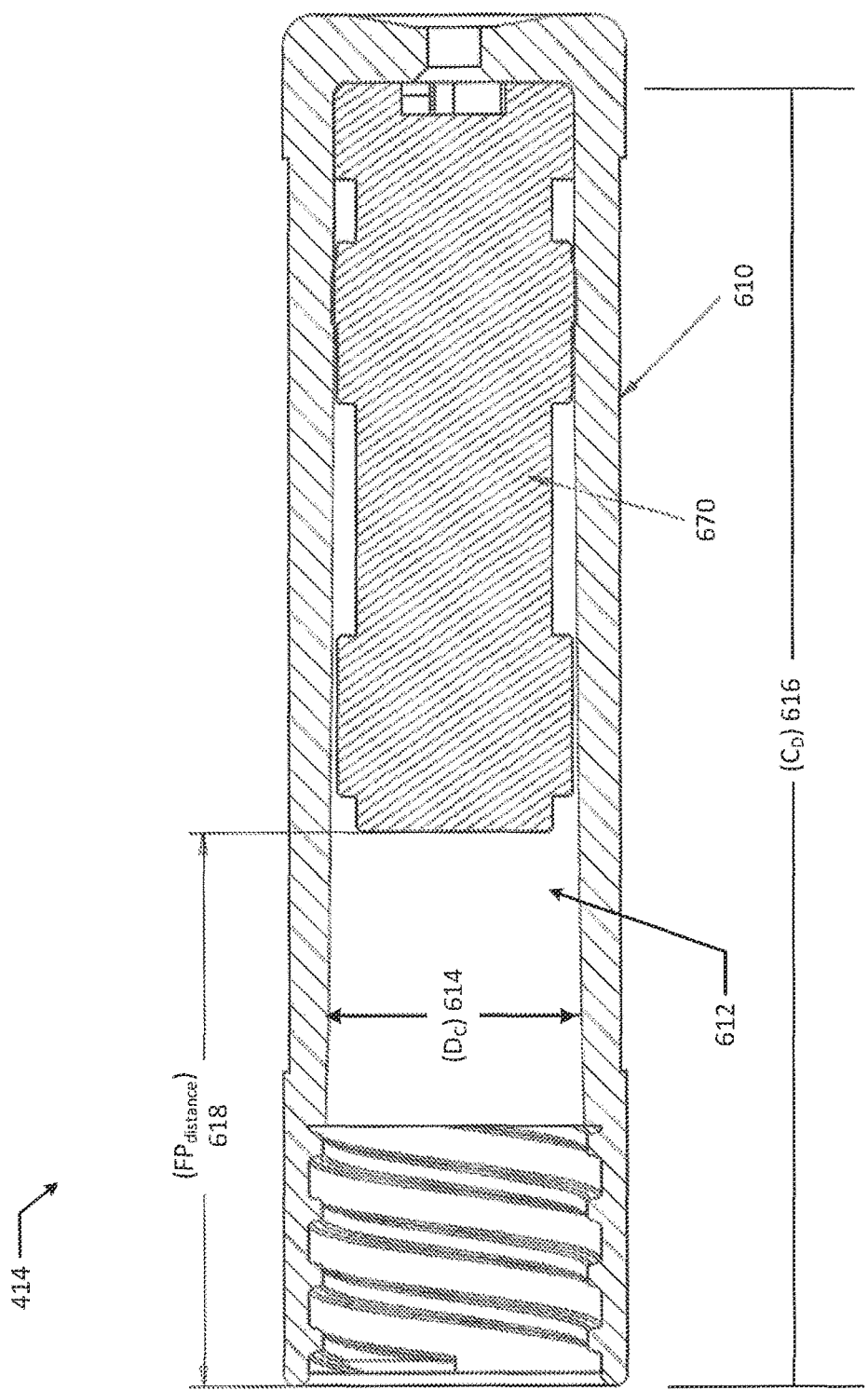
FIG. 10B is an elevated cross-sectional view of an example spray tip subassembly according to the present disclosure.

FIGS. 10A and 10B illustrate the spray tip subassembly 414. At the distal end of the device, the two sealant components and gas stream are mixed within a spray tip subassembly 414, which includes a spray tip body 610 and an insert 670. The threaded plug 412 facilitates removable connection of the spray tip subassembly 414 to the outer cannula 420 or the malleable collar 470 depending on the configuration of the fluid conveyance subassembly 140. By design, the threaded plug 412 features a taper to seal against an inner surface of the spray tip body 610, preventing leakage of the pressurized fluid mixture. The fluid mixture is mixed by way of a tip insert 670. In an example, the tip insert 670 is non-removably assembled into the spray tip body 610 via a press fit. A swirl chamber or spin chamber geometry (discussed in more detail below) is provided as part of the tip insert 670, imparting rotation of the fluid mixture as it exits the spray tip subassembly 414.

The tip body 610 may be a hollow body that forms a cavity 612. The size and shape of the cavity 612 along with the size and shape of insert 670 may be selected to optimize the mixing volume and the mixing characteristics of the spray tip subassembly 414. The cavity 640 may have a cavity diameter ($D_C$) 614 and a cavity depth ($C_D$) 616 (see FIGS. 11A and 11B). Additionally, the tip insert 670 has a volume ($V_I$) and the cavity 612 has a volume ($V_C$), where the difference between the cavity volume ($V_C$) and the insert volume ($V_I$) creates a mixing volume ($V_M$) of the spray tip subassembly 414. Adjusting the size, shape and geometry of the components of the spray tip subassembly 414 adjusts the size of the mixing volume ($V_M$) as well as the geometry of the created mixing chamber. As further illustrated in FIG. 10B, the size and shape of the cavity 612 along with the size and shape of insert 670 may be selected to adjust the mixing characteristics of the spray tip subassembly 414. For example, the geometry of the tip body 610 and insert 670 may be selected to provide an optimal fluid path distance ($FP_{distance}$) 618 before the fluids hit a first contact surface 620 of the insert 670 to start turbulence and mixing. Adjusting the fluid path distance ($FP_{distance}$) 618 along with the geometry of the tip body 610 and insert 670 may increase or decrease the turbulence created in the spray tip subassembly 414.

Tip Body

Figures 11A, 11B:
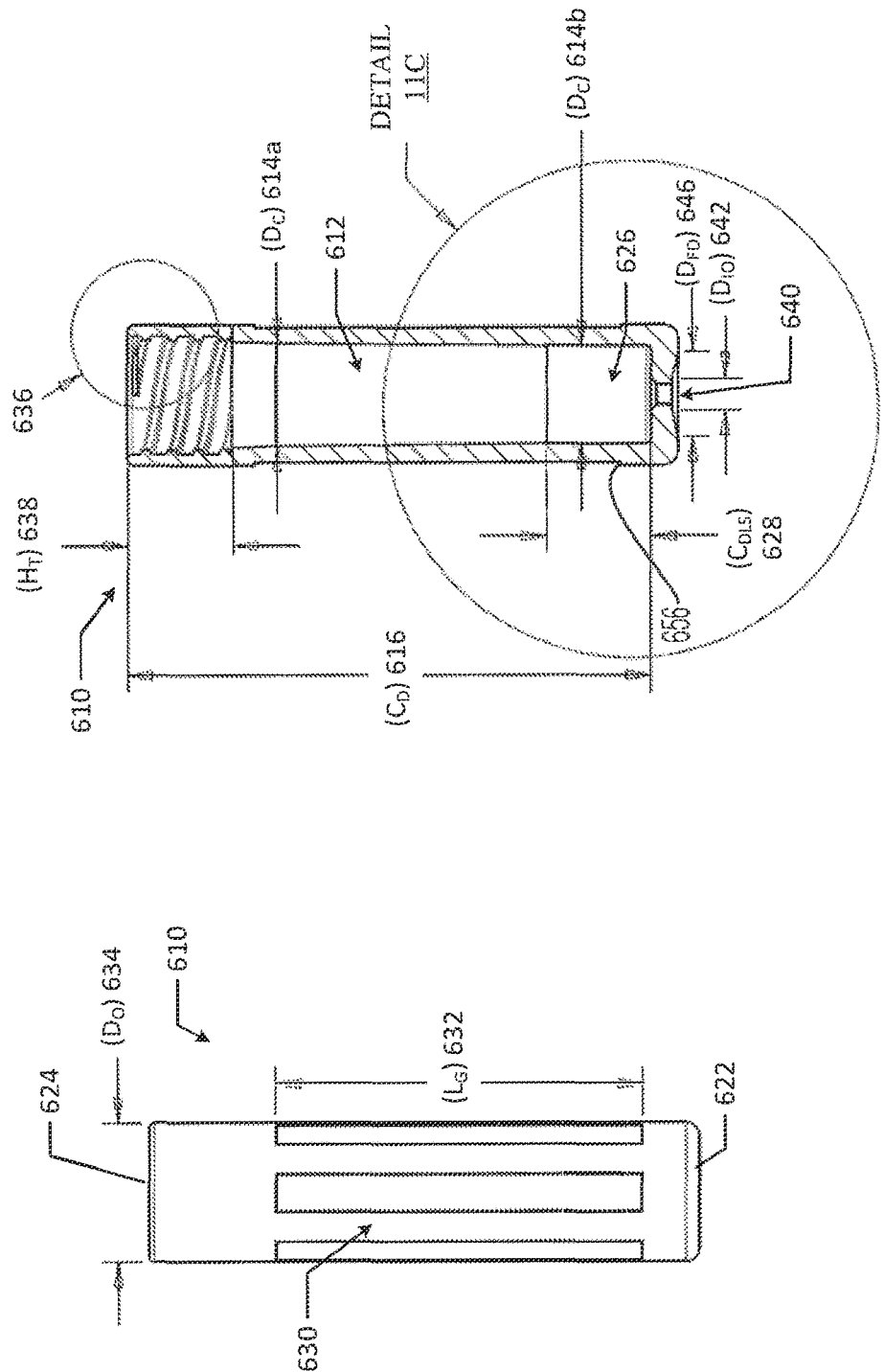
FIG. 11A is an elevated side view of an example spray tip body according to the present disclosure.
FIG. 11B is an elevated cross-sectional view of an example spray tip body according to the present disclosure.
Figure 11C:
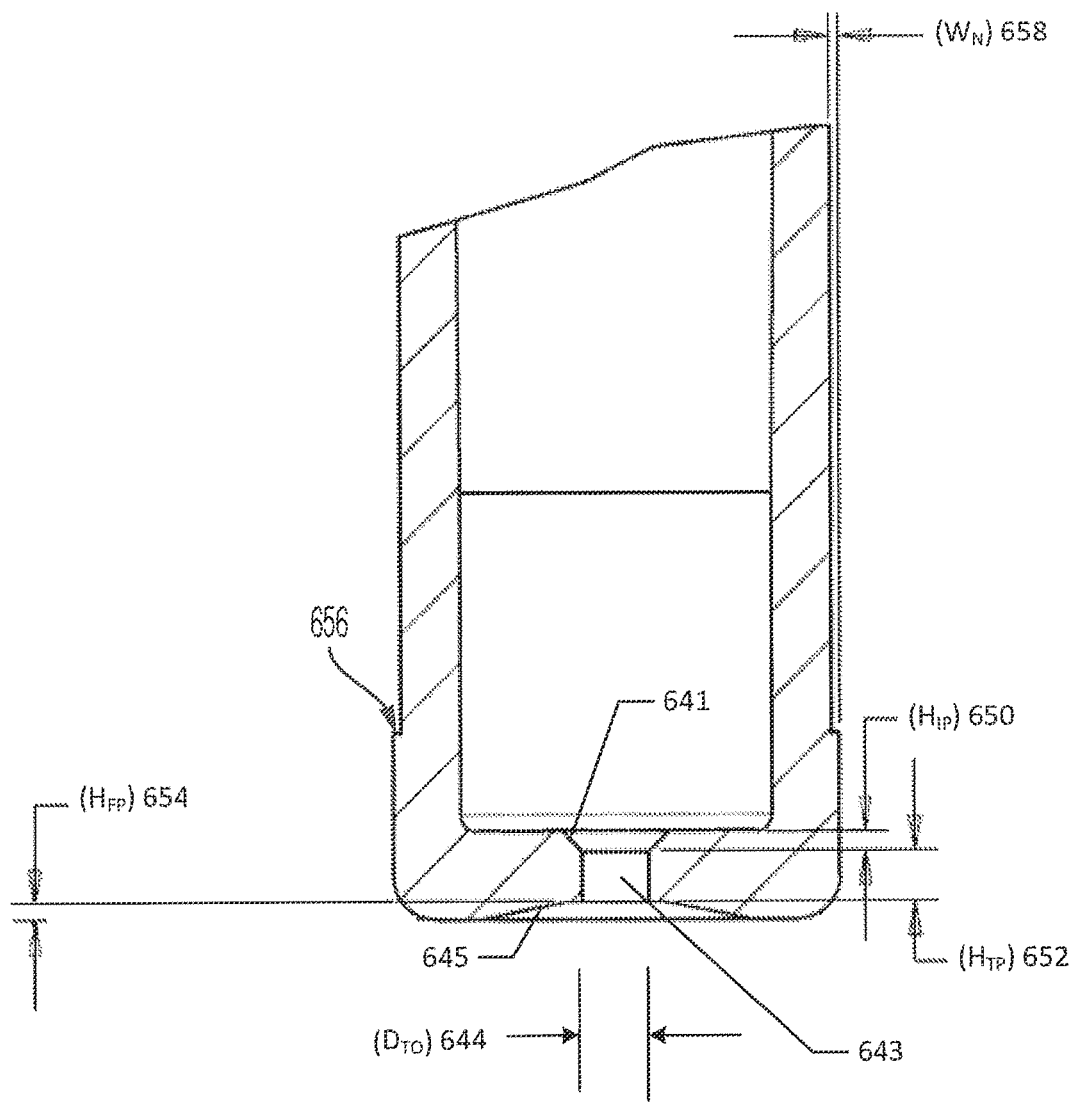
FIG. 11C is a partial view of Detail-11C of the elevated cross-sectional view of FIG. 11B.

FIGS. 11A, 11B, and 11C illustrate various views of the tip body 610. The tip body 610 may be generally cylindrical and hollow, thereby forming cavity 612 with a wall thickness of approximately 0.4 mm. As illustrated in FIG. 11B, the cavity 612 may be generally cylindrical. In some instances, the cavity 612 may be tapered such that the initial cavity diameter ($D_C$) 614a near a proximal end 624 of the tip body 610 is larger than a final cavity diameter ($D_C$) 614b near a distal end 622 of the tip body 610. The cavity diameter ($D_C$) 614a may start at approximately 4 mm and may gradually reduce as the cavity extends towards the distal end 622 of the tip body 610 until reaching a cavity diameter ($D_C$) 614b of approximately 3.7 mm. In the illustrated example, the last section 626 of the cavity 612 may have a constant cavity diameter ($D_C$) 614b. The last section 626 may have a depth ($C_{DLS}$) 628 of approximately 4 mm.

As noted above, the systems 100A, 100B may include one pre-threaded spray tip subassembly 414 and one or more replacement spray tip subassembly 414 that can be exchanged with the original pre-threaded spray tip subassembly 414 if the original spray tip becomes clogged during use. To assist with the removal and re-attachment of a respective spray tip subassembly 414, the tip body 610 may include a gripping portion 630. The gripping portion 630 may include ridges, protrusions, grooves, a textured surface, or other surface finish or surface geometry that aids with gripping the tip body 610. In the illustrated example in FIG. 11A, the gripping portion 630 may have a gripping length ($L_G$) 632, which may be approximately 14 mm. The distal end 622 of the tip body 610 may also include a small notch 656 that protrudes from an outside wall of the tip body 610 by a notch width ($W_N$) 658. The notch 656 may be present on the last 2 mm of the tip body 610 and may have a notch width ($W_N$) 658 of approximately 0.1 mm. The notch 656 may further assist a user in removing the spray tip subassembly 414.

As noted above, the tip body 610 may be generally cylindrical with an outside diameter ($D_O$) 634. In an example, the outside diameter ($D_O$) 634 is approximately 5.3 mm. Additionally, the threaded portion 636 may have a height ($H_T$) 638, where the height ($H_T$) 638 of the threaded portion 636 is approximately 4 mm.

As illustrated in FIGS. 11B and 11C, the tip body 610 also includes an orifice or outlet 640 with an initial outlet diameter (DR)) 642 associated with an initial outlet portion 641, a transition outlet diameter ($D_{TO}$) 644 associated with a transition outlet portion 643, and a final outlet diameter ($D_{FO}$) 646 associated with a final outlet portion 645. Similarly, each of the initial outlet portion 641, the transition outlet portion 643 and final outlet portion 645 may have associated heights ($H_{IP}$) 650, ($H_{IP}$) 652 and ($H_{FP}$) 654 respectively. The height ($H_{IP}$) 650 of the initial outlet portion 641 may be approximately 0.23 mm. The height ($H_{TP}$) 652 of the transition outlet portion 643 may be approximately 0.6 mm. Additionally, the height ($H_{FP}$) 654 of the final outlet portion 645 may be approximately 0.2 mm. The transition outlet diameter ($D_{TO}$), taken along with the swirl chamber geometry described below, may critically govern the width and uniformity of the resulting spray pattern. The geometry (e.g., heights and diameters) of the outlet portions may be configured to produce a preferred spray geometry or based on the materials used in the systems 100A, 100B.

Tip Insert

The tip insert 670 acts as a static mixing element within the spray tip subassembly 414. The tip insert 670 is illustrated in more detail in FIGS. 12A and 12B, which illustrates that the insert 670 has a generally cylindrical body or trunk 700 with a plurality of mixing protrusions 702 (e.g., mixing protrusions 702a-d are visible in FIG. 12A). The mixing protrusions in the illustrated example are triangular in shape with a base length ($L_{BASE}$) 704 and an internal angle ($\beta$) 706. The base length ($L_{BASE}$) 704 may be approximately 2.9 mm long and the internal angle ($\beta$) 706 may be approximately 60 degrees. The mixing protrusions 702 may be evenly spaced about the tip insert 670. In the illustrated example, the mixing protrusions 702 are spaced apart by a spacing ($S_{ME}$) 703 (e.g., spacing 703a, 703b, and 703c). The spacing ($S_{ME}$) 703 may be approximately 0.5 mm.

In an example, the plurality of mixing protrusions 702 may be positioned around the cylindrical trunk 700. In the illustrated example, the tip insert 670 includes three pairs of protrusions 720 in a staggered cross pattern such that the first set of protrusions (protrusions 702a and the other protrusion opposite 702a, but not visible in FIG. 12A) forms a "T" near the proximal end 734, and the next set of protrusions 702 (e.g., protrusions 702b and 702c) may be oriented in a different circumferential position about the tip insert 670. In an example, the second set of mixing protrusions 702 may be oriented 90 degrees from the first set. In an example, the mixing protrusions 720 may be oriented at different circumferential positions (e.g., 30 degrees, 45 degrees, etc.)

The cylindrical trunk 700 has a diameter ($D_B$) 710 and a height ($H_B$) 712. The body mixing diameter ($D_{BM}$) 714, which is the diameter of the tip insert 670 including the mixing protrusions 702, may be approximately 3.6 mm.

In an example, one or more of the mixing protrusions 702 may include a retention feature 720, which may be a protrusion, barb, or notch that creates a tight friction fit between the tip insert 670 and the tip body 610. In an example, the retention feature(s) 720 may be crush ribs that ensure the insert 670 does not dislodge from the tip body 610 over the shelf life of the device or during use and that also ensure the tip insert 670 is able to withstand the pressure built by the fluid inside the swirl chamber (described in more detail below). The retention features 720 may result in the insert 670 having an overall width (Retention) 795 of approximately 3.8 mm, which is larger than the diameter ($D_C$) 614b (referring back to FIG. 11B) by approximately 0.1 mm. The friction fit of the retention feature(s) 720 is further illustrated in FIG. 10B, which shows that a portion of the tip insert 670 is oversized for the corresponding cavity 612 of the tip body 610.

Figure 12A:
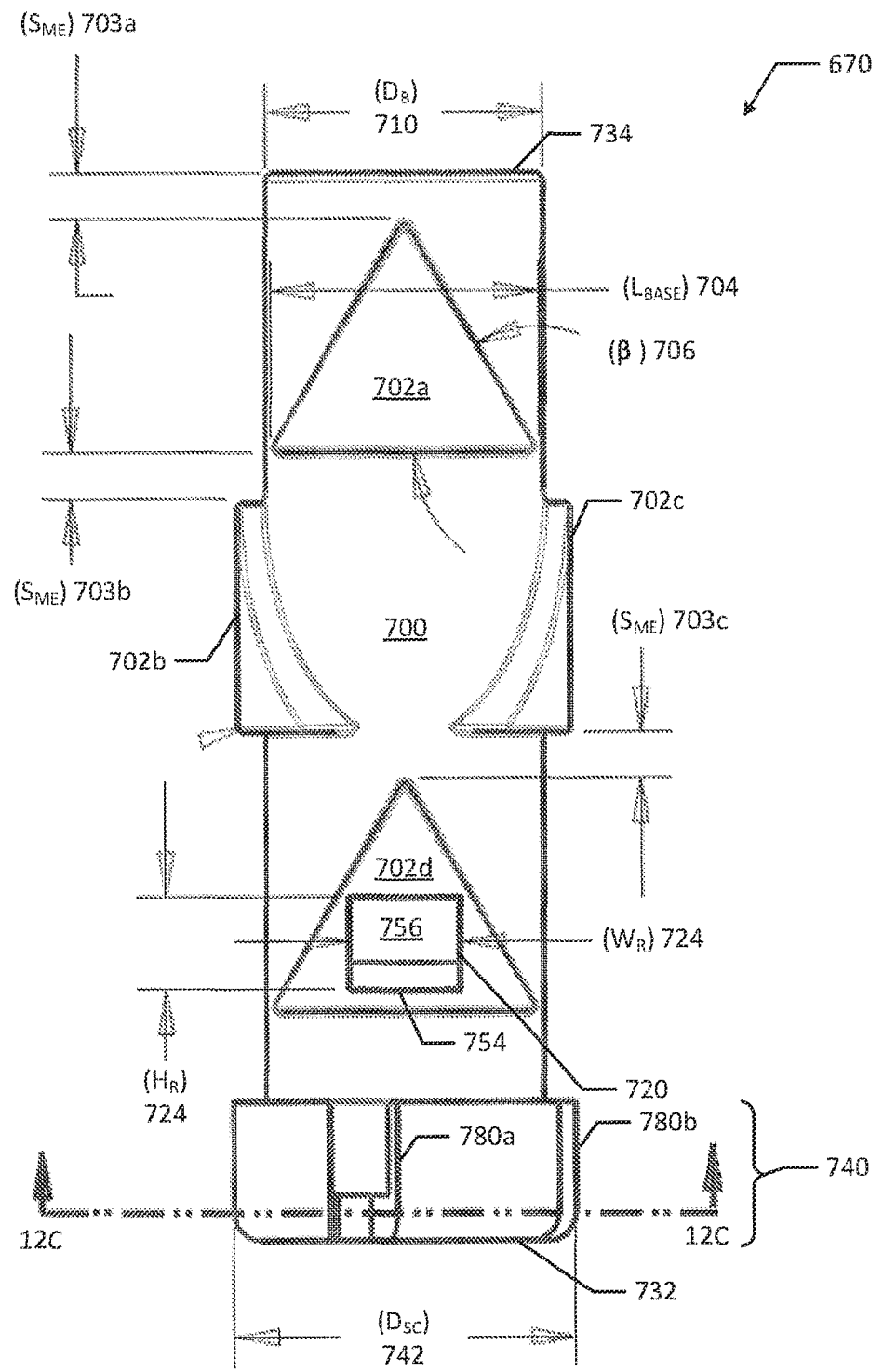
FIG. 12A is an elevated side view of an example spray tip insert according to the present disclosure.
Figure 12B:
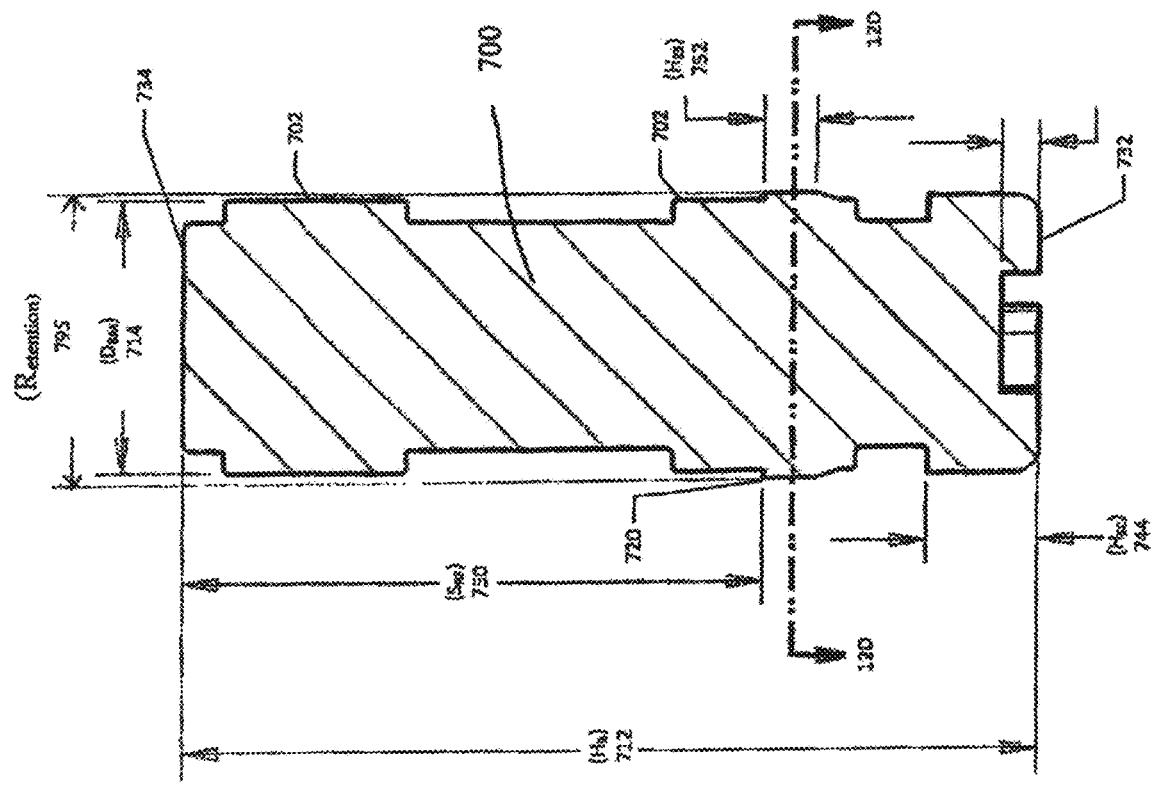
FIG. 12B is an elevated cross-sectional view of an example spray tip insert according to the present disclosure.
Figure 12D:
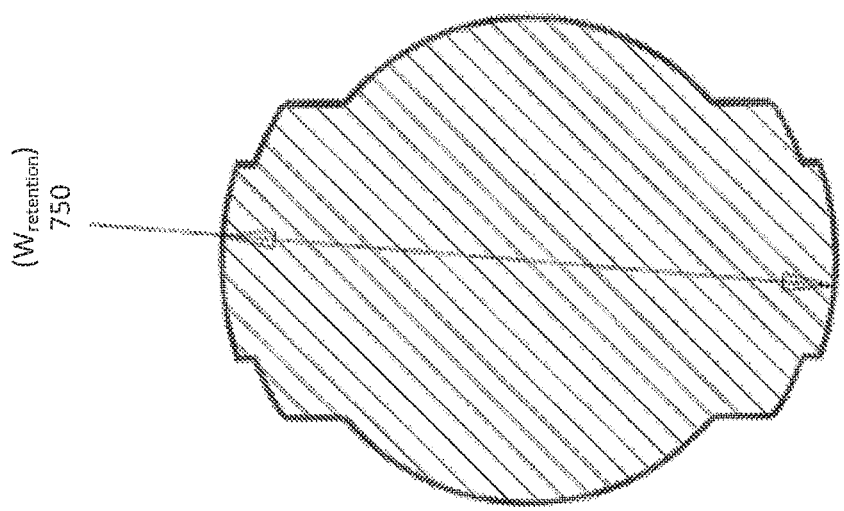
FIG. 12D is an elevated cross-sectional view taken along line 12D-12D of FIG. 12B.

In the illustrated example, the retention feature 720 is a rectangular structure with a retention height ($H_R$) 722 and a retention width ($W_R$) 724. In one embodiment, the retention height ($H_R$) 722 may be approximately 1.0 mm and a retention width ($W_R$) 724 may be approximately 1.2 mm. In the illustrated example, the retention feature 720 is spaced from the proximal end 734 of the tip insert 670 at a spacing ($S_{RF}$) 750, which may be approximately 7.8 mm. Additionally, the retention feature 720 may include a sloped profile that aids in alignment while installing via friction fit with the tip insert 670 as the tip insert 670 is press fit into tip body 610. As illustrated in FIGS. 12A and 12B, the retention feature 720 may have a sloped portion 754 and a flat portion 756, where the flat portion has an engagement surface with a height ($H_{ES}$) 752.

The tip insert 670 may have a proximal end 734 and a distal end 732 closest to the orifice or outlet 640 of tip body 610. The mixing tip insert 670 may have a blunt or flat fluid contact surface at the proximal end 734, which may be the first surface of the tip insert 670 that the multi-component sealant encounters. Additionally, the tip insert 670 may include a swirl chamber portion 740 near the distal end 732 of the tip insert 670. The swirl chamber portion may have a diameter ($D_{SC}$) 742 of approximately 3.7 mm and a height ($H_{SC}$) 744 of approximately 1.5 mm. The geometry (e.g., height and diameter) of the swirl chamber may be configured to produce a preferred spray geometry or based on the materials used in the systems 100A, 100B.

As discussed above, the mixing tip insert 670 may have a blunt or flat fluid contact surface at the proximal end 734. For example, the contact surface may be the first surface that both fluids contact and flow around, which may initially create turbulence in the spray tip subassembly 414, and where mixing of the fluids begins. It should be appreciated that other mixing geometries may be used, for example, the tip insert 670 may include helical, triangular or rectangular features, etc. Additionally, other lattice or matrix type mixing structures may be used. Additionally, the mixing structure may be omitted altogether, for example, in the case of use with a sealant requiring limited mixing before application.

As the gas and two-component sealant is pushed through the applicator or device (e.g., system 100A, 100B), the various components of the sealant and gas enter the spray tip subassembly 414 and start mixing within the cavity 612 due to interactions with the tip insert 670. As more fluid (e.g., gas and sealant) enters the spray tip subassembly 414, the mixed fluid is pushed from the cavity 612 through the outlet orifice 630 of the tip body 610. Prior to exiting through the outlet orifice 630, the fluid travels through a swirl chamber 800, illustrated in more detail in FIG. 12C.

In an example, the spray tip 414, spray tip insert 470, and threaded plug 412 components may be composed of a radiopacified resin to allow visualization under x-ray imaging (for example, 20% weight loading of Barium Sulfate).

Swirl Chamber

Figure 12C:
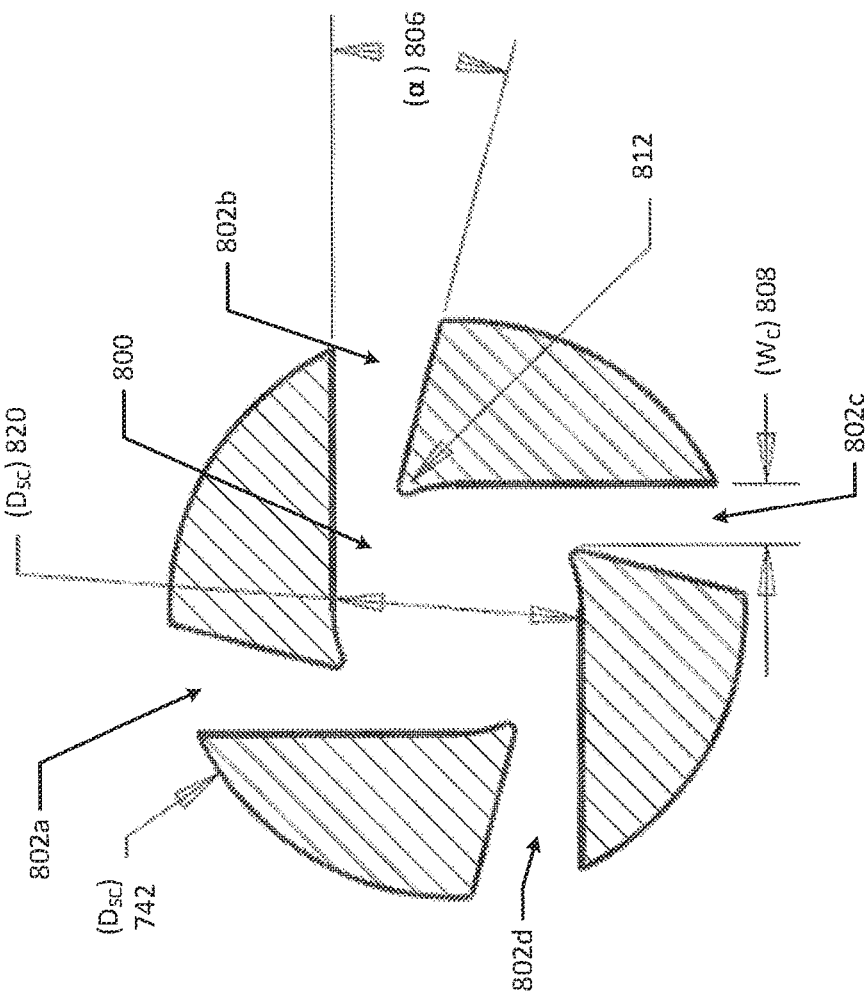
FIG. 12C is an elevated cross-sectional view taken along line 12C-12C of FIG. 12A.

Referring back to FIG. 12A (and also visible in FIG. 10A), the tip insert 670 includes channels 780 (e.g., channels 780a and 780b visible in FIG. 12A) formed within the swirl chamber portion 740. The channels 780 route the mixed fluid towards the distal end 732 of the tip insert and into corresponding horizontal channels 802 of the swirl chamber 800, as illustrated in FIG. 12C. The horizontal channels 802 serve as feeder channels that route the mixed fluid tangentially to the swirl chamber 800, which may also be referred to as a spin chamber.

The channels 802 or passageways may narrow as the channels 802 approach the swirl chamber 800. For example, each channel 802 may narrow at a constant rate or angle (a) 806, which may be approximately 15 degrees. As the channels 802 reach the swirl chamber, the channels 802 may have a channel width ($W_C$) 808 of approximately 0.4 mm and a channel depth of approximately 0.5 mm. The channels 802 may have trapezoidal cross sections that gradually reduces in cross-sectional area as the channels 802 approach the swirl chamber 800 of the tip body 610. The reduced cross-sectional area increases the velocity of the fluid entering the swirl chamber 800. As the pressurized fluid mixture enters the swirl chamber 800, the increase in the velocity and angular/tangential approach caused by the channels 802 advantageously forms a vortex, which improves mixing and nozzle performance at the spray orifice 630.

The quantity of channels 780 and 802 may depend on the preferred spray geometry or materials used in the spray tip subassembly 414. For example, the quantity of channels 780 and 802 may be determined based on the viscosity and the preferred volumetric flow rate of the fluid entering the swirl chamber 800. In the illustrated example shown in FIG. 12C, the swirl chamber 800 is fed by four channels 802. For example, four feeder channels 802 may be more effective compared to other channel configuration when used together with higher viscosity fluid such as fibrinogen from a fibrin sealant product.

The swirl chamber 800 and corresponding channels 802 may include rounded corners to aid in moldability. For example, the edges 812 where a channel 802 meets the swirl chamber 800 may be rounded with a radius of approximately 0.05 mm.

The diameter of the swirl chamber ($D_{SC}$) 820 may be approximately 1.6 mm. Additionally, the diameter of the swirl chamber ($D_{SC}$) 820, the geometry of channels 780 and 802, along with other features of the spray tip subassembly 414 may control the velocity of the fluid exiting the spray tip. As discussed above, the insert 670 has a retention feature(s) 720, such as crush ribs that ensures that the insert 670 does not dislodge from the tip body 610 during storage or use.

Mixing

As noted above, the syringe 130 may be a multi-chamber syringe that includes multiple chambers or containers (e.g., first and second fluid containers, such as syringes). The syringe 130 may contain reactive fluids. For example, the syringe 130 may include a first fluid and a second fluid. The fluids may react to create a sealant or adhesive, such as a biological tissue sealant. Due to the reactivity of fluids, they are separately stored in different chambers or containers within syringe 130, and the fluid separation is maintained through the various system components until a desired mixing point within the removable spray tip subassembly 414. Particularly reactive multi-component fluids have a tendency to form clots soon after fluid paths join and mix within the applicator. For example, for reactive solutions such as biological tissue sealants, the dwell time to clot formation can be short, and in many cases just seconds. Therefore, it is advantageous to maintain separation of the fluids up until the desired mixing point to prevent premature clotting. Additionally, it is advantageous to provide a removable or detachable spray tip subassembly 414, which can be replaced if clogging occurs during or between uses.

The geometry of the insert 670, and more specifically, the diameter of the insert 670 as well as the geometry of mixing protrusions 702 may control the cross-sectional area that the fluid stream passes by as the fluid stream travels through the spray tip subassembly 414. The geometry may also control the velocity of the fluid and the injection pressure needed to pass through the spray tip subassembly 414. The mixing protrusions 702 may create turbulence in the fluid path allowing the different fluid streams to mix and create a combined fluid stream before entering the swirl chamber 800. In an example, the quantity of mixing protrusions 702 as well as other geometrical considerations of the tip body 610 and tip insert 670 may be determined based on the fluid physical properties (e.g., viscosity, density, etc.) and the level of mixing needed prior to entering the swirl chamber 800.

The systems 100A, 100B disclosed herein advantageously produce a well-mixed reactive sealant formulation that exits the spray tip subassembly 414 with a uniform spray pattern to rapidly cover a target surgical site.

Components—Connections

It should be appreciated that many of the components described herein may be component parts that can be assembled together. For example, each component of the systems 100A, 100B may be removably attached to the other such that each component may be disassembled and reassembled. Additionally, components may be bonded together via chemical fasteners. Chemical fasteners may include, for example, adhesives, chemical bonds, weld bonds or moldings suitable for securing components. For example, each of the components illustrated in FIGS. 5A, 5B and 5C may be attached together, coupled together or connected via a threaded fitting, snap-fit, adhesive, or any other suitable fastener such that each component is connected and maintains fluid communication from the syringe 130 to the detachable spray tip subassembly 414. In other examples component parts, may instead be molded as a single piece.

Assembly

For a rigid device configuration, and more specifically when assembling the fluid conveyance subassembly 140, the sealant tubes 410 are cut to length and bonded to the threaded plug 412. For example the sealant tubes 410 may be bonded to the threaded plug 412 by applying a small amount of adhesive, such as cyanoacrylate, onto the outer surface of the sealant tube 410 and inserting the sealant tube 410 into the tube accepting portions 907 (which may also be referred to as tube bond pockets) of the threaded plug 412.

After the adhesive sets, a small amount of adhesive may be applied on the outer surface of the threaded plug 412 before inserting the proximal end of the threaded plug 412 into the outer cannula's 420 distal end until a flange of the threaded plug 412 is flush with the end of the outer cannula 420. Once again, after allowing the adhesive to set, a small amount of adhesive may be applied to an outer surface of the proximal end of the outer cannula 420 (opposite the threaded plug) and the Y-connector distal component 430 may be inserted into the cannula 420.

When inserting the Y-connector distal component 430, the components should be aligned such that the sealant passageways of the threaded plug 412 lay in-plane with the horizontal plane of the Y-connector distal component 430. After the adhesive sets, adhesive may be applied to the outer surface of the free sealant tube ends, which may then be inserted into the bosses 434 of the Y-connector proximal component 432. Then, check valves 450 may be attached to the female Luers of the Y-connector proximal component 432. Next, the gas filter 310 may be attached to the female Luer on the bottom of the Y-connector distal component 430.

A similar assembly process is performed for a malleable device configuration. However, instead of inserting the threaded plug 412 into the outer cannula 420, the threaded plug 412 is instead inserted into the malleable collar 470. Then, a small amount of adhesive is applied to the outer surface of one end of the malleable tube 460, which is then inserted into the malleable collar 470. When assembling, the stainless steel wire may be facing downward.

Next, adhesive is applied to the outer surface of the free end of the malleable tube 460, which is then inserted into the outer cannula 420. The insertion depth may be governed by the exposed length of the malleable tube 460. When correctly positioned, the gap between the malleable collar 470 and the outer cannula 420 may be, for example, 45 mm. Then, adhesive is applied to the outer surface of the proximal end of the outer cannula 420, which is then inserted into the Y-connector distal component 430. The remaining assembly steps follow the same pattern discussed above with respect to the rigid device assembly.

For the spray tip assembly, assembly starts by firmly inserting the spray tip insert 470 into the spray tip body 410 with the swirl chamber 800 geometry facing downward. The insert 470 distal face should be completely flush with the tip body 410. Then, the spray tip 414 is threaded onto the threaded plug 412 until the proximal end is flush with the flange on the plug 412.

When assembling the applicator device or systems 100A, 100B the right-hand-side casing may be laid on a flat surface. Then, a gas cartridge is installed into the gas activator knob using a small amount of adhesive. The gas activator knob is threaded clockwise to partially thread the gas cartridge into the valve assembly. In an example, the gas activator knob is threaded for three turns to ensure the cartridge is well-engaged with the valve, but not punctured.

Then the gas tube is connected to the valve barb outlet and a Luer barb is installed on the free end of the gas tube. Then, the Luer barb is connected to the relief valve by a Luer lock connection. The relief valve's male Luer slip connector is inserted into the gas filter on the fluid conveyance subassembly. The gas activator knob is positioned into the corresponding groove on the casing and the gas tube and relief valve are routed to make with their corresponding features on the casing.

Then, the fluid conveyance subassembly is installed into its corresponding groove on the casing. The linkage is assembled; and one or more of the pins, trigger, and/or torsional springs may then be installed (depending on the embodiment of the system being assembled). Then, the opposite side of the casing is aligned and attached to the other casing with screws.

Aspects of the subject matter described herein may be useful alone or in combination with one or more other aspects described herein.

To the extent that any of these aspects are mutually exclusive, it should be understood that such mutual exclusivity shall not limit in any way the combination of such aspects with any other aspect whether or not such aspect is explicitly recited. Any of these aspects may be claimed, without limitation, as a system, method, apparatus, device, medium, etc.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

What is claimed is:

1. An applicator for mixing and dispensing a multi-component fluid, the applicator comprising:
    a fluid conveyance subassembly in fluid communication with a syringe, wherein the syringe houses at least two different sealant components;
    a housing;
    a gas cartridge disposed inside the housing;
    a gas valve assembly disposed inside the housing, the gas valve assembly in fluid communication with the gas cartridge and the fluid conveyance subassembly, the gas valve assembly including a flow restrictor orifice sized to control or reduce gas flow from the gas cartridge to the fluid conveyance subassembly; a gas filter disposed inside the housing and along a fluid path of gas flowing from the gas valve assembly to the fluid conveyance subassembly; and a relief valve disposed inside the housing and along a fluid path of gas flowing from the gas valve assembly to the fluid conveyance subassembly;
    a trigger configured to actuate the gas valve assembly; and
    a detachable spray tip in fluid communication with the fluid conveyance subassembly, the detachable spray tip configured to dispense the multi-component fluid out of the applicator.

2. The applicator of claim 1, wherein the detachable spray tip includes:
    a body including an open end, a closed end, and an inner cavity extending between the open end and the closed end, wherein the closed end has an inner facing surface and an outlet orifice.

3. The applicator of claim 2, wherein the body has a cylindrical shape.

4. The applicator of claim 2, wherein the detachable spray tip includes:
    a spray tip insert housed within the body, the insert including a plurality of outwardly projecting mixing protrusions radially spaced at different positions between a proximal end and a distal end of the spray tip insert, the spray tip insert and the body forming a mixing chamber within the inner cavity.

5. The applicator of claim 4, wherein the detachable spray tip includes:
    a swirl chamber formed from the spray tip insert and the inner facing surface of the body, wherein the spray tip insert is configured to cause the multi-component fluid to mix within the mixing chamber before entering the swirl chamber and exiting through the outlet orifice.

6. The applicator of claim 1, wherein the housing is shaped to form a handle.

7. The applicator of claim 1, wherein the gas valve assembly includes:
    a valve body having a lower portion shaped to engage with the gas cartridge.

8. The applicator of claim 7, wherein the flow restrictor orifice is disposed at a side port of the valve body.

9. The applicator of claim 8, wherein the valve body has an inner cavity extending at least between the lower portion of the valve body and the side port of the valve body to transport gas flowing from the gas cartridge to the flow restrictor orifice.

10. The applicator of claim 8, wherein the gas valve assembly includes:
    a valve barb shaped to connect with the valve body, the valve barb extending away from the valve body at the side port, wherein the flow restrictor orifice is disposed inside the valve barb.

11. The applicator of claim 7, wherein the gas cartridge is a threaded gas cartridge, and wherein the valve body is shaped to threadingly engage with the threaded gas cartridge.

12. The applicator of claim 11, wherein the trigger is further configured to actuate the syringe.

13. The applicator of claim 7, wherein the gas valve assembly includes:
    a puncture needle connected to the valve body at the lower portion of the valve body, the puncture needle extending toward the gas cartridge to engage the valve body with the gas cartridge by puncturing the gas cartridge.

14. The applicator of claim 13, wherein the puncture needle is threaded into the valve body at the lower portion of the valve body to affix the puncture needle to the valve body.

15. The applicator of claim 14, wherein the gas valve assembly includes:
    a poppet disposed between the puncture needle and the valve body, wherein the puncture needle is shaped to capture the poppet when the puncture needle is affixed to the valve body.

16. The applicator of claim 7, wherein the gas valve assembly includes:
    a valve stem installed into an upper bore of the valve body, wherein the valve stem is configured to move the gas valve assembly from a closed state to an open state by depressing the valve stem.

17. The applicator of claim 1, further comprising:
    a gas tube disposed inside the housing and extending between the gas valve assembly and the relief valve to transport gas flowing out of the gas valve assembly and into the relief valve.

* * * * *